(12) United States Patent
Firestone et al.

(10) Patent No.: US 6,613,879 B1
(45) Date of Patent: Sep. 2, 2003

(54) FAP-ACTIVATED ANTI-TUMOUR COMPOUNDS

(75) Inventors: Raymond A. Firestone, Stamford, CT (US); Wolfgang J. Rettig, Biberach (DE); Martin Lenter, Ulm (DE); Stefan Peters, Ingelheim (DE); Pilar Garin-Chesa, Biberach (DE); Juergen Mack, Biberach (DE); Dietmar Leipert, Ingelheim (DE); John E. Park, Biberach (DE); Leila A. Telan, Somerville, MA (US)

(73) Assignees: Boehringer Ingelheim Pharma KG, Ingelheim (DE); Boehringer Ingelheim Pharmaceuticals, Inc., Ridgefield, CT (US)

( * ) Notice: Subject to any disclaimer, the term of this patent is extended or adjusted under 35 U.S.C. 154(b) by 0 days.

(21) Appl. No.: 09/553,800

(22) Filed: Apr. 21, 2000

Related U.S. Application Data

(60) Provisional application No. 60/134,136, filed on May 14, 1999.

(51) Int. Cl.$^7$ .................................................. C07K 5/08
(52) U.S. Cl. ...................... 530/330; 530/329; 530/330; 548/535; 514/17; 514/18; 514/19; 514/152
(58) Field of Search ............................ 514/17–19, 152; 530/329, 330, 331; 548/535

(56) References Cited

U.S. PATENT DOCUMENTS

| | | | | |
|---|---|---|---|---|
| 3,915,800 A | * | 10/1975 | Kang | .................... 435/101 |
| 4,703,107 A | | 10/1987 | Monsigny et al. | .......... 530/330 |
| 5,206,221 A | * | 4/1993 | Lipsky et al. | ................ 514/19 |
| 5,776,892 A | * | 7/1998 | Counts et al. | ................ 514/11 |
| 6,271,342 B1 | * | 8/2001 | Lerchen | ...................... 530/322 |

FOREIGN PATENT DOCUMENTS

| | | |
|---|---|---|
| EP | 0 255 341 | 2/1988 |
| EP | 0 624 377 | 11/1994 |
| WO | WO 97/12624 | 4/1997 |
| WO | WO 97/14416 | 4/1997 |
| WO | WO 97/45117 | 12/1997 |
| WO | WO 98/04277 | 2/1998 |
| WO | WO 98/13059 | 4/1998 |
| WO | WO 00/33888 | 6/2000 |
| WO | WO 00/64486 | 11/2000 |

OTHER PUBLICATIONS

Abstract—1998–231397 of Patent Application DE 19640970.

De Marre, Anne; et al, Synthesis and evaluation of macromolecular prodrugs of mitomycin C, Journal of Controlled Release, Special Issue 36 (1995) Sep., Nos. 112, Amsterdam, NL, p. 87–97.

Nichifor, Marieta, et al; Chemical and enzymatic hydrolysis of dipeptide derivatives of 5–fluorouracil, Journal of Controlled Release 47 (1997) 271–281, XP 000689098.

John E. Park. et al; Fibroblast Activation Protein, a Dual Specificity Serine Protease Expressed in Reactive Human Tumor Stromal Fibroblasts, Journal of Biological Chemistry, Dec. 17, 1999, pp. 36505–36512, vol. 274, No. 51.

P. Calieti,et al; Preparation and Properties of Monomethoxy Poly(Ethylene Glycol) Doxorubicin Conjugates Linked by an Amino Acid or a peptide as Spacer, 2193 II Farmaco, 48 (1993) Jul., No. 7, Rom, It. pp 919–932.

\* cited by examiner

*Primary Examiner*—Christopher S. F. Low
*Assistant Examiner*—David Lukton
(74) *Attorney, Agent, or Firm*—Robert P. Raymond; Anthony P. Bottino; Alan R. Stempel

(57) ABSTRACT

The invention relates to a prodrug that is capable of being converted into a drug by the catalytic action of human fibroblast activation protein (FAPα), said prodrug having a cleavage site which is recognised by FAPα, and said drug being cytotoxic or cytostatic under physiological conditions.

14 Claims, 5 Drawing Sheets

Z-Gly-Pro-Dox + CD8FAP

Z-Gly-Pro-Dox + buffer

FAP-ACTIVATED ANTI-TUMOUR COMPOUNDS

RELATED APPLICATIONS

Figure 1:
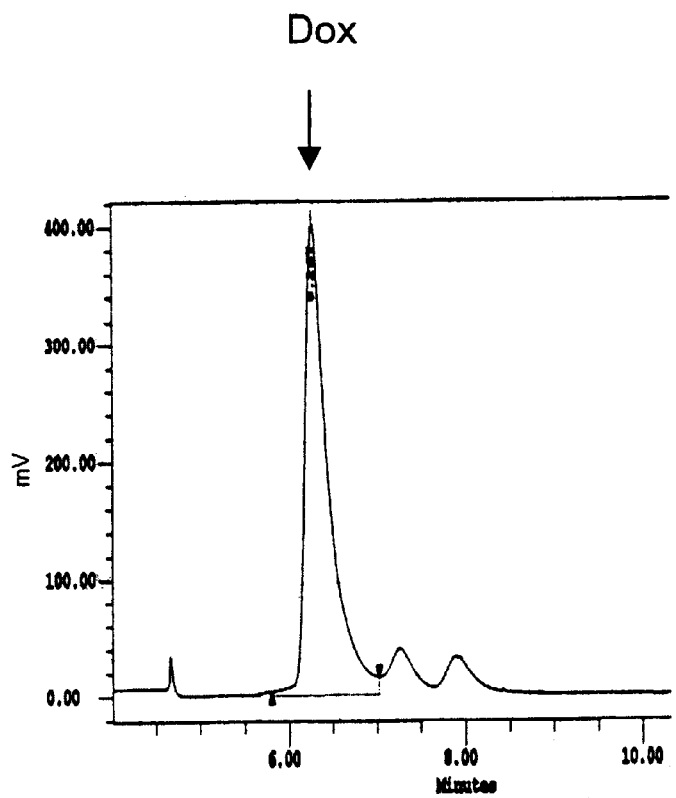
Figure 1:
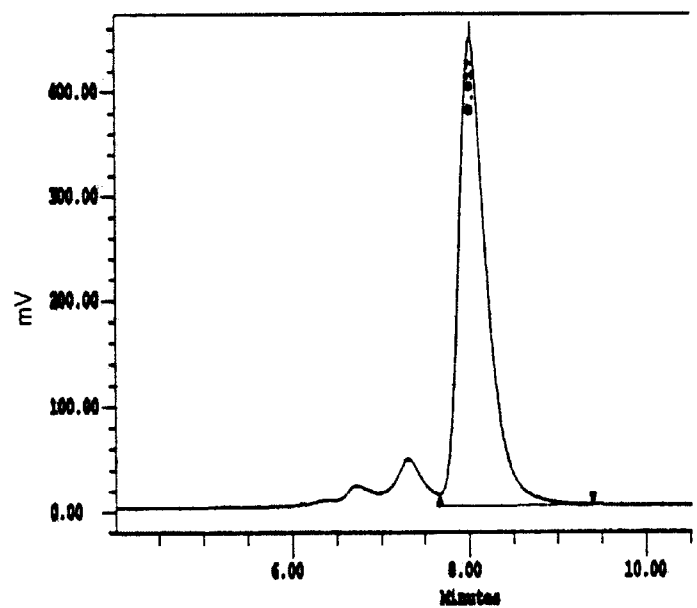

This application claims priority to U.S. Provisional Application serial No. 60/134,136 filed May 14, 1999.

FIELD OF THE INVENTION

The present invention relates to the field of tumour treatment by administration of a prodrug that is converted into a drug at the site of the tumour. In particular, the invention relates to prodrugs which may be converted into a drug by the catalytic action of FAPα, their manufacture and pharmaceutical use.

BACKGROUND AND PRIOR ART

The human fibroblast activation protein (FAPα) is a M, 95,000 cell surface molecule originally identified with monoclonal antibody (mAb) F19 (Rettig et al. (1988) *Proc. Natl. Acad. Sci. USA* 85, 3110–3114; Rettig et al. (1993) *Cancer Res.* 53, 3327–3335). The FAPα cDNA codes for a type II integral membrane protein with a large extracellular domain, trans-membrane segment, and short cytoplasmic tail (Scanlan et al. (1994) *Proc. Natl. Acad. Sci. USA* 91, 5657–5661; WO 97/34927). FAPα shows 48% amino acid sequence identity to the T-cell activation antigen CD26, also known as dipeptidyl peptidase IV (DPPIV; EC 3.4.14.5), a membrane-bound protein with dipeptidyl peptidase activity (Scanlan et al., loc. cit.). FAPα has enzymatic activity and is a member of the serine protease family, with serine 624 being critical for enzymatic function (WO 97/34927). Work using a membrane overlay assay revealed that FAPα dimers are able to cleave Ala-Pro-7-amino-4-trifluoromethyl coumarin, Gly-Pro-7-amino-4-trifluoromethyl coumarin, and Lys-Pro-7-amino-4-trifluoromethyl coumarin dipeptides (WO 97/34927).

FAPα is selectively expressed in reactive stromal fibroblasts of many histological types of human epithelial cancers, granulation tissue of healing wounds, and malignant cells of certain bone and soft tissue sarcomas. Normal adult tissues are generally devoid of detectable FAPα, but some foetal mesenchymal tissues transiently express the molecule. In contrast, most of the common types of epithelial cancers, including >90% of breast, non-small-cell lung, and colorectal carcinomas, contain FAPα-reactive stromal fibroblasts (Scanlan et al., loc. cit.). These FAPα$^+$ fibroblasts accompany newly formed tumour blood vessels, forming a distinct cellular compartment interposed between the tumour capillary endothelium and the basal aspect of malignant epithelial cell clusters (Welt et al. (1994) *J. Clin. Oncol.* 12(6), 1193–1203). While FAPα$^+$ stromal fibroblasts are found in both primary and metastatic carcinomas, the benign and premalignant epithelial lesions tested (Welt et al., loc. cit.), such as fibroadenomas of the breast and colorectal adenomas, only rarely contain FAPα$^+$ stromal cells. Based on the restricted distribution pattern of FAPα in normal tissues and its uniform expression in the supporting stroma of many malignant tumours, clinical trials with $^{131}$I-labeled mAb F19 have been initiated in patients with metastatic colon carcinomas (Welt et al., loc. cit.).

For new cancer therapies based on cytotoxic or cytostatic drugs, a major consideration is to increase the therapeutic index by improving the efficacy of cancerous tissue killing and/or reducing the toxicity for normal tissue of the cytotoxic or cytostatic agents. To increase specificity of tumour tissue killing and reduce toxicity in normal tissues, trigger mechanisms can be designed so that the toxic agents synthesised in their prodrug or inactive forms are rendered active when and where required, notably in the cancerous tissues (Panchal (1998) *Biochem. Pharmacol.* 55, 247–252). Triggering mechanisms may include either exogenous factors such as light or chemicals or endogenous cellular factors, such as enzymes with restricted expression in cancer tissues. Another concept, that has been further elaborated, is called 'antibody-directed enzyme prodrug therapy' (ADEPT) or 'antibody-directed catalysis' (ADC) (Huennekens (1994) *Trends Biotechnol.* 12, 234–239; Bagshawe (1994) *Clin. Pharmacokinet.* 27, 368–376; Wang et al. (1992) *Cancer Res.* 52, 4484–4491; Sperker et al. (1997) *Clin. Pharmacokinet.* 33(1), 18–31). In ADEPT, an antibody directed at a tumour-associated antigen is used to target a specific enzyme to the tumour site. The tumour-located enzyme converts a subsequently administered prodrug into an active cytotoxic agent. The antibody-enzyme conjugate (AEC) binds to a target antigen on cell membranes or to free antigen in extracellular fluid (ECF). A time interval between giving the AEC and prodrug allows for the AEC to be cleared from normal tissues so that the prodrug is not activated in the normal tissues or blood. However, some disadvantages of ADEPT are related to the properties of the AEC (Bagshawe, loc. cit.). For example, in humans, only a small fraction of the administered dose of the targeting ACE binds to tumour tissue and the remainder is distributed through body fluids from which it is cleared with significant time delays. Even very low concentrations of targeted enzyme can catalyse enough prodrug to have toxic effects because plasma and normal ECF volumes are much greater than those of tumour ECF. The AEC may also be immunogenic, thus preventing repeat administration, in many instances.

The International patent applications WO 97/12624 and WO 97/14416 disclose oligopeptides including the following penta- and hexapeptide (SEQ.ID.NOs.: 151 and 177: hArg-Tyr-Gln-Ser-Ser-Pro; hArg-Tyr-Gln-Ser-Pro;), comprising amino acid sequences, which are recognized and proteolytically cleaved by free prostate specific antigen (PSA) and therapeutic agents which comprise conjugates of such oligopeptides and known therapeutic or cytotoxic agents. These oligopeptide conjugates which comprise at least one glutamineserine moiety are useful for treatment of prostate cancer only.

The problem underlying the present invention was to provide methods and means for improving normal tissue tolerability of cytotoxic or cytostatic agents with known efficacy against a broad range of tumour tissues.

DISCLOSURE OF THE INVENTION

The present invention relates to enzyme-activated anti-tumour compounds. In particular, the invention provides prodrugs that are capable of being converted into drugs by the catalytic action of endogenous fibroblast activating protein alpha (FAPα) shown to reside in human cancer tissues. Preferably, a prodrug of the present invention is capable of being converted into a drug by the catalytic action of FAPα, said prodrug having a cleavage site which is recognised by FAPα, and said drug being cytotoxic or cytostatic against cancer cells under physiological conditions.

In the context of this invention, a "drug" shall mean a chemical compound that may be administered to humans or animals as an aid in the treatment of disease. In particular, a drug is an active pharmacological agent.

The term "cytotoxic compound" shall mean a chemical compound which is toxic to living cells, in particular a drug that destroys or kills cells. The term "cytostatic compound" shall mean a compound that suppresses cell growth and multiplication and thus inhibits the proliferation of cells. Examples for cytotoxic or cytostatic compounds suitable for the present invention are anthracycline derivatives such as doxorubicin, analogs of methotrexate such as methothrexate, pritrexime, trimetrexate or DDMP, melphalan, analogs of cisplatin such as cisplatin, JM216, JM335, bis(platinum) or carboplatin, analogs of purines and pyrimidines such as cytarbine, gemcitabine, azacitidine, 6-thioguanine, flurdarabine or 2-deoxycoformycin, and analogs of other chemotherapeutic agents such as 9-aminocamptothecin, D,L-aminoglutethimide, trimethoprim, pyrimethamine, mitomycin C, mitoxantrone, cyclophosphanamide, 5-fluorouracil, extramustine, podophyllotoxin, bleomycin or taxol.

A "prodrug" shall mean a compound that, on administration, must undergo chemical conversion by metabolic processes before becoming an active pharmacological agent. In particular, a prodrug is a precursor of a drug. In the context of the present invention, the prodrug is significantly less cytotoxic or cytostatic than the drug it is converted into upon the catalytic action of FAPα. The expert knows methods of determining cytotoxicity of a compound, see e.g. example 6 herein, or Mosmann ((1983) *J. Immun. Meth.* 65, 55–63). Preferably, the prodrug is at least three times less cytotoxic as compared to the drug in an in vitro assay.

A "drug being cytostatic or cytotoxic under physiological conditions" shall mean a chemical compound which is cytostatic or cytotoxic in a living human or animal body, in particular a compound that kills cells or inhibits proliferation of cells within a living human or animal body.

A "prodrug having a cleavage site which is recognised by FAPα" shall mean a prodrug which can act as a substrate for the enzymatic activity of FAPα. In particular, the enzymatic activity of FAPα can catalyse cleavage of a covalent bond of the prodrug under physiological conditions. By cleavage of this covalent bond, the prodrug is converted into the drug, either directly or indirectly. Indirect activation would be the case if the cleavage product of the FAPα catalysed step is not the pharmacologically active agent itself but undergoes a further reaction step, e.g. hydrolysis, to become active. More preferably, the cleavage site of the prodrug is specifically recognised by FAPα, but not by other proteolytic enzymes present in the human or animal body. Also preferably, the cleavage site is specifically recognised by FAPα, but not by proteolytic enzymes present in human or animal body fluids, especially plasma. In a particularly preferred embodiment, the prodrug is stable in plasma, other body fluids, or tissues, in which biologically active FAPα is not present or detectable. Preferably, in an in vitro assay as carried out in Example 7 herein, more than 50%, more preferably more than 80%, more preferably more than 90% of the prodrug are still present in a solution containing 10% (v/v) of human plasma after 8 h at 37° C. The cleavage site should most preferably be specific for FAPα. In a preferred embodiment, the cleavage site comprises a L-proline residue which is linked to a cytotoxic or cytostatic drug via an amide bond. An example of this class is a doxorubicin-peptide conjugate. FAPα may catalyse the cleavage of a peptidic bond between the C-terminal amino acid residue of the peptide, which is preferably L-proline, and the cytotoxic or cytostatic compound.

Preferred compounds show at least 10% conversion to free drug, under standard conditions listed below. More preferred are compounds that show at least 20% conversion to free drug, under standard conditions. Even more preferred are compounds that show at least 50% conversion to free drug, under standard conditions. In this context, standard conditions are defined as follows: Each compound is dissolved in 50 mM Hepes buffer, 150 mM NaCl, pH 7.2, at a final concentration of 5 μM and incubated with 100 ng CD8FAPα (see example 4) for 24 hours at 37° C. Release of free drug by CD8FAPα is determined as described in example 5.

Preferably, the present invention relates to a compound of formula (I)

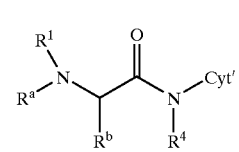

(I)

or a pharmaceutically acceptable salt thereof, wherein
$R^1$ represents an amino alkanoyl, an oligopeptidoyl, in particular a di- or tripeptidoyl group, the N-terminal amino function of which may be attached to a capping group;
$R^1$ and $R^b$ together with the interjacent N—C group form an optionally substituted, optionally benzo- or cyclohexano-condensed 3- to 7-membered saturated or unsaturated heterocyclic ring, in which one or two $CH_2$ groups may also be replaced by NH, O or S,
$R^4$ represents H, $C_1$–$C_6$-alkyl, $C_3$–$C_8$-cycloalkyl, aryl or heteroaryl; and
Cyt' represents the residue of a cytotoxic or cytostatic compound,
with the proviso that,
N2-acetyl-L-homoarginyl-L-tyrosyl-L-glutaminyl-L-seryl-N-[2,3,6-trideoxy-1-O-[(1S,3S)-1,2,3,4,6,11-hexahydro-3,5,12-trihydroxy-3-(hydroxyacetyl)-10-methoxy-6,11-dioxo-1-naphthacenyl]-.alpha.-L-lyxo-hexopyranos-3-yl]-L-prolinamide; and
N2-acetyl-L-homoarginyl-L-tyrosyl-L-glutaminyl-L-seryl-L-seryl-N-[2,3,6-trideoxy-1-O-[(1S,3S)-1,2,3,4,6,11-hexahydro-3,5,12-trihydroxy-3-(hydroxyacetyl)-10-methoxy-6,11-dioxo-1-naphthacenyl]-.alpha.-L-lyxo-hexopyranos-3-yl]-L-prolinamide are excluded.

Particularly preferred are those compounds of formula I, wherein $R^1$ is a residue of formula Cg—A, Cg—B—A or Cg—(D)$_m$—B—A, in which Cg represents a hydrogen atom, or a capping group selected from the group consisting of $R^5$—CO, $R^5$—O—CO—, $R^5$—NH—CO—, $R^5$—$SO_2$— or $R^5$—, wherein $R^5$ is an optionally substituted $C_1$–$C_6$-alkyl, $C_3$–$C_8$-cycloalkyl, aryl, aralkyl or heteroaryl group;

preferably Cg is an acetyl, benzoyl, D-alanyl, (R)—$H_2NCH(CH_3)$—, or $H_2NCOCH_2CH_2$— substituent or another capping group for the protection of the N-terminal amino function;

A, B and D each independently represent moieties derived from amino carboxylic acids of the formula —[$NR^6$—$(X)_p$—CO]— wherein X represents $CR^7R^8$ and wherein $R^6$, $R^7$ and $R^8$ each independently represent a hydrogen atom, an optionally substituted $C_1$–$C_6$-alkyl, $C_3$–$C_8$-cycloalkyl, aryl or heteroarylgroup, and p is 1, 2, 3, 4, 5; or A, B and D each independently represent moieties derived from cyclic amino carboxylic acids of formula

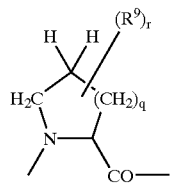

wherein
$R^9$ represents $C_1$–$C_6$-alkyl, OH, or $NH_2$,
m is an integer from 1 to 10,
q is 0, 1 or 2; and
r is 0, 1 or 2.

Furthermore preferred are those compounds of formula I, wherein $R^6$, $R^7$ and $R^8$ each independently represent a hydrogen atom or $CH_3$—, $CH_3CH_2$—, $CH_3CH_2CH_2$—, $(CH_3)_2CH$—, $CH_3CH_2CH_2CH_2$—, $(CH_3)_2CHCH_2$—, $CH_3CH_2CH(CH_3)$—, $(CH_3)_3C$—, $HOCH_2$—, $CH_3CH(OH)$—, $CH_3CH(OH)CH_2CH_2$—, $HOCH_2CH_2CH_2CH_2$—, $H_2NCH_2CH_2CH_2$—, $H_2NCH_2CH_2CH_2CH_2$—, $H_2NCH_2CH(OH)CH_2CH_2$—, $H_2NC(=NH)NHCH_2CH_2CH_2$—, $HSCH_2$—, $CH_3SCH_2CH_2$—, $HOOCCH_2$—, $HOOCCH_2CH_2$—, $H_2NC(=O)CH_2$—, $H_2NC(=O)CH_2CH_2$—, benzyl, para-hydroxy-benzyl,

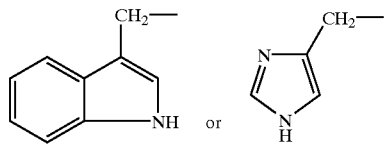

cyclohexyl, phenyl, p is 1, and wherein the configuration at $CR^7R^8$ can be R or S; if $R^7$ is other than H, then $R^8$ is preferably H; $R^6$ is preferably H; if p is greater than one, $R^7$ and $R^8$ are preferably H;

Another preferred embodiment of the present invention are those compounds of formula I, wherein the heterocyclic ring formed by $R^a$, $R^b$ and the interjacent N—C is substituted by $R^2$ and $R^3$, wherein $R^2$ and $R^3$ each independently represent a hydrogen or halogen atom or a $C_1$–$C_6$-alkyl, $C_1$–$C_6$-alkylamino, di-$C_1$–$C_6$-alkylamino, $C_1$–$C_6$-alkoxy, thiol, $C_1$–$C_6$-alkylthio, oxo, imino, fomyl, $C_1$–$C_6$-alkoxy carbonyl, amino carbonyl, $C_3$–$C_8$-cycloalkyl, aryl, or heteroaryl group.

Unless indicated otherwise, the simple stereoisomers as well as mixtures or racemates of the stereoisomers are included in the invention.

"$C_1$–$C_6$-alkyl" generally represents a straight-chained or branched hydrocarbon radical having 1 to 6 carbon atoms.

The term "optionally substituted" as used hereinabove or hereinbelow with respect to a group or a moiety refers to a group or moiety which may optionally be substituted by one or several halogen atoms, hydroxyl, amino, $C_1$–$C_6$-alkyl-amino, di- $C_1$–$C_6$-alkyl-amino, $C_1$–$C_6$-alkyl-oxy, thiol, $C_1$–$C_6$-alkyl-thio, =O, =NH, —CHO, —COOH, —$CONH_2$, —NHC(=NH)$NH_2$, $C_3$–$C_8$-cycloalkyl, aryl, or heteroaryl substituents, which may be identical to one another or different.

The following radicals may be mentioned by way of example:

Methyl, ethyl, propyl, 1-methylethyl (isopropyl), butyl, 1-methylpropyl, 2-methylpropyl, 1,1-dimethylethyl, n-pentyl, 1-methylbutyl, 2-methylbutyl, 3-methylbutyl, 1,1-dimethyl-propyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2methyl-propyl, $HOCH_2$—, $CH_3CH(OH)$—, $CH_3CH(OH)CH_2CH_2$—, $HOCH_2CH_2CH_2CH_2$—, $H_2NCH_2CH_2CH_2$—, $H_2NCH_2CH_2CH_2CH_2$—, $H_2NCH_2CH(OH)CH_2CH_2$—, $H_2NC(=NH)NHCH_2CH_2CH_2$—, $HSCH_2$—, $CH_3SCH_2CH_2$—, $HOOCCH_2$—, $HOOCCH_2CH_2$—, $H_2NC(=O)CH_2$—, $H_2NC(=O)CH_2CH_2$—, benzyl, para-hydroxy-benzyl,

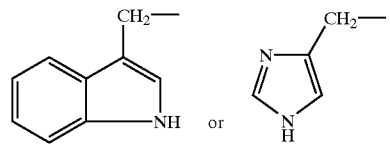

If a $C_1$–$C_6$-alkyl group is substituted, the substituents are preferably hydroxyl, amino, dimethylamino, diethylamino, thiol, methyl-thiol, methoxy, ethoxy, =O, =NH, —CHO, —COOH, —$COOCH_3$, —$COOCH_2CH_3$, —$CONH_2$, —NHC(=NH)$NH_2$, cyclohexyl, phenyl, benzyl, para-hydroxy-benzyl,

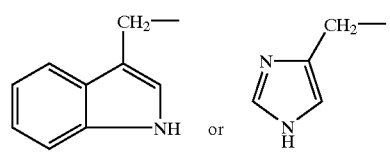

If $C_1$–$C_6$-alkyl is substituted with aryl or heteroaryl, $C_1$–$C_6$-alkyl is preferably $C_1$, more preferably a methylene group.

The terms "amino alkanoyl" and "oligopeptidoyl" including "di- or tripeptidoyl" as used hereinabove or hereinbelow with respect to radical $R^1$ describe a radical in which an amino acid or an oligomer comprising up to 12, preferably 2 or 3 amino acid moieties is attached C-terminally to the nitrogen atom of the heterocyclic ring via an amid bond.

A person of ordinary skill in the chemistry of amino acids and oligopeptides will readily appreciate that certain amino acids may be replaced by other homologous, isosteric and/or isolectronic amino acids wherein the biological activity of the original amino acid or oligopeptide has been conserved upon modification. Certain unnatural and modified natural amino acids may also be utilized to replace the corresponding natural amino acid. Thus, for example, tyrosine may be replaced by 3-iodotyrosine, 2- or 3-methyltyrosine, 3-fluorotyrosine.

The term "capping group" as used hereinabove or hereinbelow with respect to a group which is attached to the N-terminal nitrogen atom of the amino alkanoyl or oligopeptidoyl group of radical $R^1$ defines a group or moiety which reduces or eliminates the enzymatic degradation of the compounds of the present invention by the action of amino peptidases which are present in the blood plasma of warm blooded animals. Suitable capping groups include $C_1$–$C_{10}$ alkanoyl, $C_6$–$C_{18}$-aryl-$C_1$–$C_{10}$-alkanoyl, $C_6$–$C_{18}$-aryl-$C_1$–$C_{10}$-alkylsulfonyl. Such capping groups also include hydrophilic blocking groups, which are chosen upon the presence of hydrophilic functionality. Such capping groups increase the hydrophilicity of the compounds of the present invention and thus enhance their solubility in aqueous media. These hydrophilicity enhancing capping groups are preferably selected from hydroxylated alkanol, polyhydroxylated alkanoyl, hydroxylated aroyl, hydroxylated arylalkanoyl, polyhydroxylated aroyl, polyhydroxylated arylalkanoyl, polyethylene glycol, glycosylates, sugars, and crown ethers.

"$C_3$–$C_8$-Cycloalkyl" generally represents cyclic hydrocarbon radical having 3 to 8 carbon atoms which may optionally be substituted by one or several hydroxyl, amino, $C_1$–$C_6$-alkyl-amino, di-$C_1$–$C_6$-alkyl-amino, $C_1$–$C_6$-alkyl, $C_1$–$C_6$-alkyloxy, thiol, $C_1$–$C_6$-alkyl-thio, =O, =NH, —CHO, —COOH, —COOCH$_3$, —COOCH$_2$CH$_3$, —CONH$_2$, —NHC(=NH)NH$_2$, or halogen substituents, which may be identical to one another or different.

"Heterocyclic ring" as used hereinabove and hereinbelow with respect to the group formed by $R^a$ and $R^b$ together with the interjacent N—C group generally represents a 3 to 7-membered, preferably 4-, 5- or 6-membered non-aromatic heterocyclic ring system, containing one nitrogen atom and optionally 1 or 2 additional heteroatoms selected from the group of nitrogen, oxygen and sulfur, which may be substituted by one or several halogen atoms or $C_1$–$C_6$-alkyl, $C_1$–$C_6$-alkylamino, di-$C_1$–$C_6$-alkylamino, $C_1$–$C_6$-alkoxy, thiol, $C_1$–$C_6$-alkylthio, oxo, imino, fomyl, $C_1$–$C_6$-alkoxy carbonyl, amino carbonyl, $C_3$–$C_8$-cycloalkyl, aryl, or heteroaryl groups, which may be identical to one another or different, and which optionally may be benzo- or cyclohexano-condensed. Such heterocyclic rings are preferably azetidine or are derived from a fully or partially hydrogenated pyrrole, pyridine, thiazole, isoxazole, pyrazole, imidazole, indole, benzimidazole, indazole, pyridazine, pyrimidine, pyrazin group. Most preferred are azetidine, pyrrolidine, 3,4-dehydropyrrolidine, piperidine, hexahydro-1H-azepine, octahydroindole, imidazolidine, thiazolidine.

If such heterocyclic ring is substituted, the substituents are preferably methyl, ethyl, propyl, 1-methylethyl (isopropyl), butyl, 1-methylpropyl, 2-methylpropyl, 1,1-dimethylethyl, droxyl, amino, dimethyl-amino, diethyl-amino, thiol, methyl-thiol, methoxy, ethoxy, —CHO, —COOH, —COOCH$_3$, —COOCH$_2$CH$_3$, or —CONH$_2$.

"Aryl" generally represents an aromatic ring system with 6 to 10, preferably 6 carbon atoms which may optionally be substituted by one or several hydroxyl, amino, $C_1$–$C_6$-alkyl-amino, di-$C_1$–$C_6$-alkyl-amino, $C_1$–$C_6$-alkyl, $C_1$–$C_6$-alkyloxy, thiol, $C_1$–$C_6$-alkyl-thio, —CHO, —OOH, —COOCH$_3$, —COOCH$_2$CH$_3$, —CONH$_2$, or halogen substituents, which may be idential to one another or different, and which optionally may be benzocondensed. Aryl subtituents may be preferably derived form benzene, preferred examples being phenyl, 2-hyroxy-phenyl, 3-hydroxy-phenyl, 4-hydroxy-phenyl, 4-amino-phenyl, 2-amino-phenyl, 3-amino-phenyl.

If aryl is substituted, the substituents are preferably methyl, ethyl, propyl, 1-methylethyl (isopropyl), butyl, 1-methylpropyl, 2-methylpropyl, 1,1-dimethylethyl, hydroxyl, amino, dimethyl-amino, diethyl-amino, thiol, methyl-thiol, methoxy, ethoxy, —CHO, —COOH, —COOCH$_3$, —COOCH$_2$CH$_3$, or —CONH$_2$.

"Heteroaryl" generally represents a 5 to 10-membered aromatic heterocyclic ring system, containing 1 to 5 heteroatoms selected from the group of nitrogen, oxygen, or sulfur, which may optionally be substituted by one or several hydroxyl, amino, $C_1$–$C_6$-alkyl-amino, di-$C_1$–$C_6$-alkyl-amino, $C_1$–$C_6$-alkyl, $C_1$–$C_6$-alkyloxy, thiol, $C_1$–$C_6$-alkyl-thio, —CHO, —COOH, COOCH$_3$, —COOCH$_2$CH$_3$, —CONH$_2$, or halogen substituents, which may be identical to one another or different, and which optionally may be benzocondensed. Heteroaryl substituents may preferably be derived from furane, pyrrole, thiophene, pyridine, thiazole, isoxazole, pyrazole, imidazole, benzofuran, thianaphthene, indole, benzimidazole, indazole, chinoline, pyridazine, pyrimidine, pyrazin, chinazoline, pyrane, purine, adenine, guanine, thymine, cytosine, uracil.

If heteroaryl is substituted, the substituents are preferably methyl, ethyl, propyl, 1-methylethyl (isopropyl), butyl, 1-methylpropyl, 2-methylpropyl, 1,1-dimethylethyl, hydroxyl, amino, dimethyl-amino, diethyl-amino, thiol, methyl-thiol, methoxy, ethoxy, —CHO, —COOH, —COOCH$_3$, —COOCH$_2$CH$_3$, or —CONH$_2$.

"Residue of a cytotoxic or cytostatic compound" means that the compound H$_2$N—Cyt', which is released upon cleavage of the amide bond shown in formula (I), is either cytotoxic or cytostatic itself, or may be converted into a cytotoxic or cytostatic compound in a subsequent step.

In the latter case, —Cyt' may be a residue of formula —L—Cyt", wherein L is a linker residue derived from a bifunctional molecule, for instance a diamine H$_2$N—L'—NH$_2$, an amino alcohol H$_2$N—L'—OH, for example p-amino-benzyl alcohol (PABOH), an amino carbonate, for example

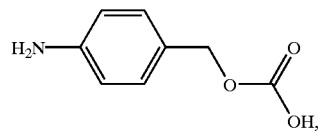

or an unnatural amino carboxylic acid. If —Cyt' is of formula —L—Cyt", the compound H$_2$N—L'—Cyt" is generated by the enzymatic cleavage of the amide bond shown in formula (I). The compound H₂N—L'—Cyt" may be cytotoxic or cytostatic itself or the linker residue cleaved off from Cyt" in a subsequent step releasing the cytotoxic or cytostatic agent. For example, the compound H₂N—L'—Cyt" may be hydrolysed under physiological conditions into a compound H₂N—L'—OH and the cytotoxic or cytostatic compound H—Cyt", which is the active therapeutic agent (In the following, only the term Cyt' is used for both Cyt' and Cyt", and only the term L is used for both L and L', for simplicity).

The pharmaceutically acceptable salts of the compounds of the present invention include the conventional non-toxic salts formed from non-toxic inorganic or organic acids. For example, such conventional non-toxic salts include those from inorganic acids such as hydrochloric acid, hydrobromic, sulfuric, sulfamic, phosphoric, nitric and the like; and the salts prepared from organic acids such as acetic, propionic, succinic, glycolic, stearic, lactic, malic, tartaric, citric, ascorbic, maleic, phenylacetic, glutamic, benzoic, salicylic, sulfanilic, oxalictrifluoroacetic and the like.

Preferred compounds of formula I are those of fomula IA (IA)

wherein $R^2$, $R^3$, $R^4$, Cyt' are as defined hereinabove, $R^1$ represents an amino alkanoyl or oligopeptidoyl group, and X—Y represents $CHR^2$—$CH_2$, $CR^2$=CH, NH—$CH_2$, $CH_2$—NH, —$CR^2$—, $CH_2$—$CHR^2$—$CH_2$; with the proviso that $R^1$ represents an amino alkanoyl, di- or tripeptidoyl group or $R^1$ represents an oligopeptidoyl having more than three amino acid moieties which does not contain a Gln-Ser amino acid sequence, in the event that X—Y represents a $CH_2$—$CH_2$ group.

Preferably the α carbon atom of the cyclic amino acid residue is racemic, i.e. of (R/S) configuration, most preferably of (S) configuration; in a particularly prefererred embodiment, the α carbon atom is of (S) configuration and $R^2$ is H. In the event that $R^2$ is OH, it is preferably in trans position.

$R^2$, $R^3$ preferably represent a hydrogen atom or a methyl, ethyl, propyl, isopropyl, phenyl, methoxy, ethoxy or hydroxy group, most preferably a hydrogen atom. $R^4$ is preferably a hydrogen atom or a methyl, ethyl, propyl, isopropyl or phenyl group, most preferably a hydrogen atom.

Particularly preferred compounds of formula IA are selected from the formulae IA1, IA2, IA3, IA4 and IA5

(IA1)

-continued (IA2)

(IA3)

(IA4)

(IA5)

H₂N—Cyt' is preferably an anthracycline derivative of formula II (II)

wherein $R^c$ represents $C_1$–$C_6$ alkyl, $C_1$–$C_6$ hydroxyalkyl or $C_1$–$C_6$ alkanoyloxy $C_1$–$C_6$ alkyl, in particular methyl, hydroxymethyl, diethoxyacetoxymethyl or buryryloxymethyl;

$R^d$ represents hydrogen, hydroxy or $C_1$–$C_6$ alkoxy, in particular methoxy;

one of $R^e$ and $R^f$ represents a hydrogen atom; and the other represents a hydrogen atom or a hydroxy or tetrahydropyrany-2-yloxy (OTHP) group.

Paricularly preferred are the following compounds of formula II:

| $R^c$ | $R^d$ | $R^e$ | $R^f$ | Cyt |
|---|---|---|---|---|
| CH₂OH | OCH₃ | H | OH | doxorubicin |
| CH₃ | OCH₃ | H | OH | daunorubicin |
| CH₂OH | OCH₃ | OH | H | epirubicin |
| CH₃ | H | H | OH | idarubicin |
| CH₂OH | OCH₃ | H | OTHP | THP |
| CH₂OH | OCH₃ | H | H | esorubicin |
| CH₂OCOCH(OC₂H₅)₂ | OCH₃ | H | OH | detorubicin |

-continued

| $R^c$ | $R^d$ | $R^e$ | $R^f$ | Cyt |
|---|---|---|---|---|
| CH₂OH | H | H | OH | carminorubicin |
| CH₂OCOC₄H₉ | OCH₃ | H | OH | |

Most preferred is doxorubicin (Dox). Other cytotoxic or cytostatic residues Cyt' may be derived for example from methotrexate, trimetrexate, pyritrexim, 5,10-dideazatetrahydrofolatepyrimetamine, trimethoprim, 10-propargyl-5,8-dideazafolate-2,4-diamino-5(3',4'-dichloropheyl)-6-methylpyrimidine, aminoglutethimide, goreserelin, melphalan, chlorambucil, analogs of other chemotherapeutic agents such as 9-aminocamtothecin (for examples see e.g. Burris HA, r. d. and S. M. Fields (1994). "Topoisomerase I inhibitors. An overview of the camptothecin analogs. [Review]." *Hematol. Oncol. Clin. North Am.* 8(2): 333–355; Iyer, L. and M. J. Ratain (1998). "Clinical pharmacology of camptothecins. [Review] [137 refs]." *Cancer Chemother. Pharmacol.* 42 Suppl: S31–S43.)

In formula (I), Cyt' may also be a biological effector molecule which either directly or indirectly effects destruction of tumour cells, like for example TNFα.

Preferred examples of amino carboxylic acids from which the A, B, and D units may be derived are glycine (Gly), or the D- or, more preferably, the L-forms of alanine (Ala), valine (Val), leucine (Leu), isoleucine (Ile), phenylalanine (Phe), tyrosine (Tyr), tryptophan (Trp), cysteine (Cys), methionine (Met), serine (Ser), threonine (Thr), lysine (Lys), arginine (Arg), histidine (His), aspartatic acid (Asp), glutamic acid (Glu), asparagine (Asn), glutamine (Gln), proline (Pro), trans-4-hydroxy-proline (Hyp), 5-hydroxy-lysine (Hyl), norleucine (Nle), 5-hydroxynorleucine, 6-hydroxynorleucine (Hyn), omithine (Orn), cyclohexylglycine (Chg), phenylglycine (Phg), glutamine (Gln), cyclohexylalanine (Cha), methionine-S-oxide (Met), β-cyclopropylalanine (Cpa), tert.-leucine (Tle), or homoserine (Hse).

Preferred compounds have the general formula (I), wherein the A unit is derived from alanine, valine (Val), leucine (Leu), isoleucine (Ile), phenylalanine (Phe), tyrosine (Tyr), tryptophan (Trp), cysteine (Cys), methionine (Met), serine (Ser), threonine (Thr), lysine (Lys), arginine (Arg), histidine (His), aspartatic acid (Asp), glutamic acid (Glu), asparagine (Asn), glutamine (Gln), proline (Pro), trans-4-hydroxy-proline (Hyp), 5-hydroxy-lysine (Hyl), norleucine (Nle), 5-hydroxynorleucine, 6-hydroxynorleucine (Hyn), ornithine (Orn), or cyclohexylglycine (Chg), phenylglycine (Phg), glutamine (Gln), cyclohexylalanine (Cha), methionine-S-oxide (Met), β-cyclopropylalanine (Cpa), tert.-leucine (Tle) or homoserine (Hse).

Particularly preferred are those compounds of formula (I), wherein $R^1$ is a group selected from the formnulae (1) to (34):

| | | | |
|---|---|---|---|
| H-Chg | (1) | H-Tle | (18) |
| H-Lys | (2) | H-Hyl | (19) |
| H-Nle | (3) | H-Hse | (20) |

-continued

| | | | |
|---|---|---|---|
| H-Ala | (4) | Cg-Gly | (21) |
| H-Hyn | (5) | Cg-Nle | (22) |
| H-Pro | (6) | Cg-Val | (23) |
| H-Phg | (7) | Cg-Met | (24) |
| H-Gln | (8) | H-Xxx-Lys | (25) |
| H-trans-Hyp | (9) | H-Xxx-Hyn | (26) |
| H-Val | (10) | H-Xxx-Pro | (27) |
| H-Cha | (11) | H-Xxx-His | (28) |
| H-Met | (12) | H-Xxx-Met | (29) |
| H-Nva | (13) | H-Xxx-Ala | (30) |
| H-Met(O) | (14) | Cg-Xxx-Hyn | (31) |
| H-β-Cpa | (15) | Cg-Xxx-Ala-Gly | (32) |
| H-Ile | (16) | Cg-(Xxx)ₘ-Xxx-Ala-Gly | (33) |
| H-Ser | (17) | Cg-(Xaa)ₘ-Xaa-Gly | (34) | wherein

Cg represents a hydrogen atom or a capping group selected from benzoyloxycarbonyl, phenylacetyl, phenylmethylsulfonyl and benzylaminocarbonyl; Xaa represents a moiety derived from an amino carboxylic acid, preferably selected form the group natural amino acids, in particular from the group consisting of Ala, Pro, Tyr, Phe, His, Ser, Thr, Hyp and Lys; and m is an integer from 1 to 6.

Preferred capping groups Cg are acetyl (Ac), succinimidyl (Suc), D-alanyl, benzyloxycarbonyl (Cbz or Z), or macromolecules such as polyethylene glycol.

Preferred anthracycline prodrugs are the compounds of formula III

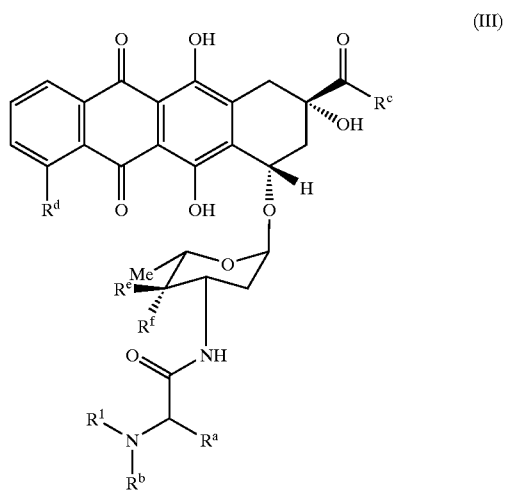

(III)

wherein $R^a$, $R^b$, $R^c$, $R^d$, $R^e$, $R^f$ and $R^1$ are as defined hereinabove.

Most preferred compounds of the invention are doxorubicin derivatives of formulae (IIIA) to (IIIF):

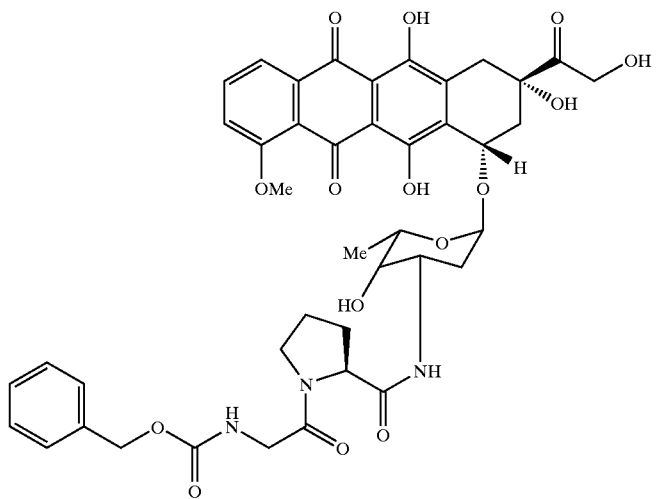
(IIIA)
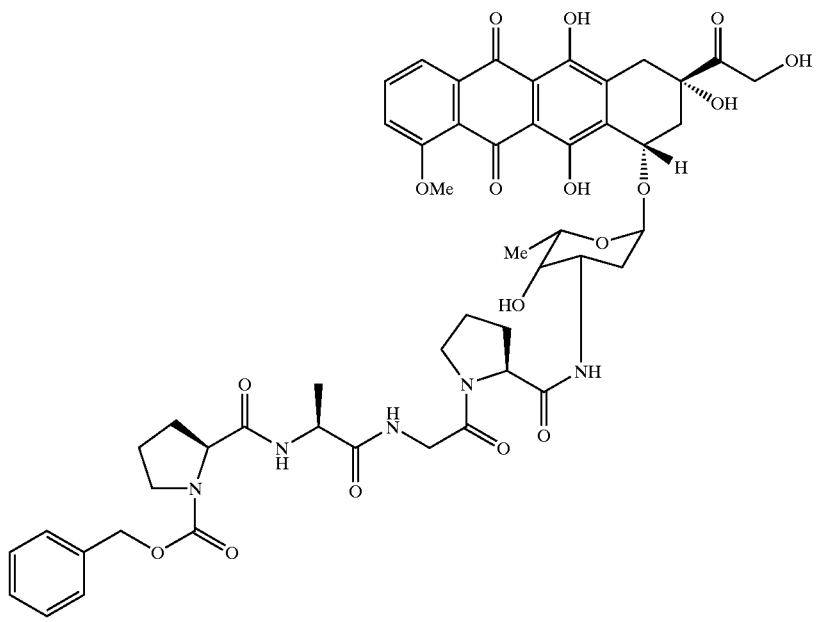
(IIIB)
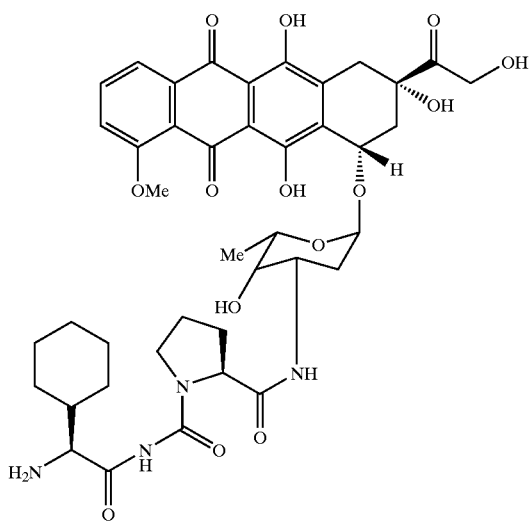
(IIIC)
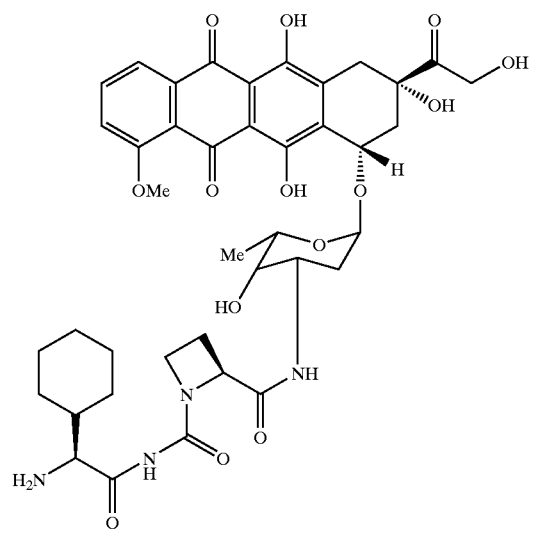
(IIID)

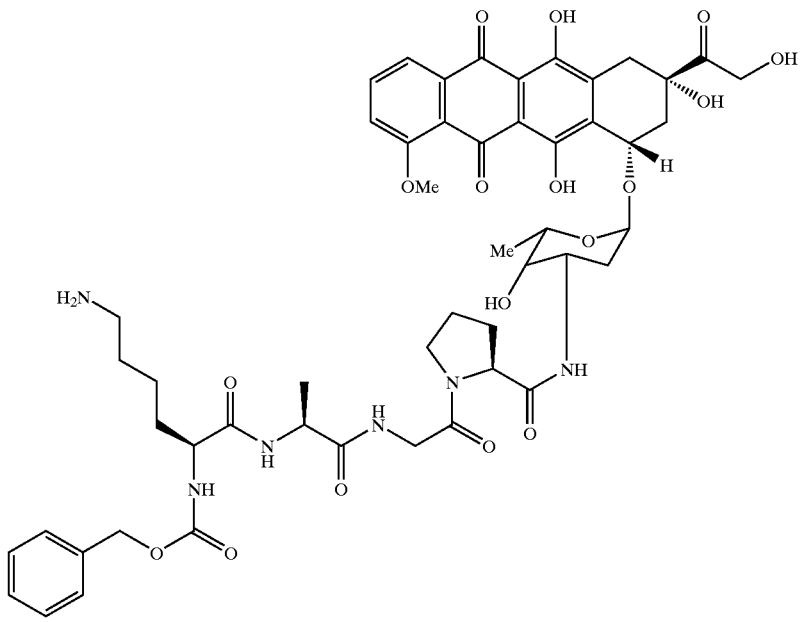

(IIIE)

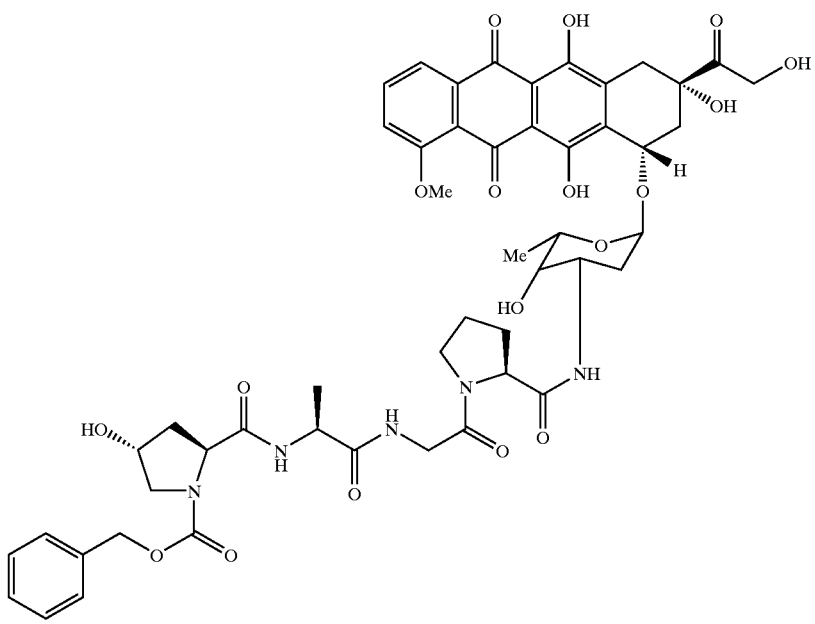

(IIIF)

If the part Cg—B—A or Cg—(D)m_B—A of formula (I) contains two or more sulfur atoms, the compound of the invention may contain one or more disulfide bonds.

One class of cytotoxic or cytostatic compounds which may be used for the present invention has a primary amino function which is available for formation of an amidic bond as shown in formula (I), like doxorubicin. In this case, a linker molecule L is not necessary. If a cytostatic or cytotoxic compound does not have such an amino function, such a function may be created in such a compound by way of chemical modification, e.g. by introducing or converting a functional group or attaching a linker molecule to the compound. A linker molecule may also be inserted between the oligomeric part (i.e. the part comprising the amino carboxylic residues) and the cytostatic or cytotoxic part of the compound of the invention to ensure or optimise cleavage of the amide bond between the oligomeric part and the cytotoxic or cytostatic part. If a linker molecule is present, i.e. in compounds containing the structure L—Cyt', the bond between L and Cyt' is preferably an amidic or ester bond. In a preferred embodiment, such a linker molecule is hydrolysed off the cytostatic or cytotoxic compound under physiological conditions after the enzymatic cleavage and thus the free cytostatic or cytotoxic compound is generated. In any case, the compound of the invention must have the property of being cleavable upon the catalytic action of FAPα and, as a direct or indirect consequence of this cleavage, releasing under physiological conditions a cytostatic or cytotoxic compound.

In a further aspect, the present invention relates to a prodrug that is capable of being converted into a drug by the catalytic action of FAPα, said prodrug having a cleavage site which is recognised by FAPα, and said drug being cytotoxic or cytostatic under physiological conditions. Such a prodrug preferably comprises an oligomeric part comprising two or more amino carboxylic residues and a cytotoxic or cytostatic part, wherein the C-terminal amino carboxylic residue of the oligomeric part is a 3- to 7-membered natural or unnatural cyclic amino acid, preferably D- or L-proline, or D- or L-hydroxyproline, and the C-terminal carboxy function is linked to the cytotoxic or cytostatic part by an amide bond which may be cleaved by the catalytic action of FAPα. The oligomeric part is preferably a peptide. Preferably, the oligomeric part comprises two, three, four, five, six, seven, eight, nine, ten, eleven, or twelve amino carboxylic acid residues, more preferably two, three, or four amino carboxylic residues. The N-terminal amino function is preferably protected by a capping group.

The compounds of the invention may be synthesized by processes known in the art (E. Wünsch, Synthese von Peptiden, in "Methoden der organischen Chemie", Houben-Weyl (Eds. E. Müller, O. Bayer), Vol. XV, Part 1 and 2, Georg Thieme Verlag, Stuttgart, 1974). For example, the compounds could be synthesized in a block synthetic fashion by condensation of the terminal carboxy function of the oligomeric part, wherein X may be OH or an activation leaving group, with the amino group of the cytotoxic or cytostatic molecule H$_2$N—Cyt' resulting in an amide formation.

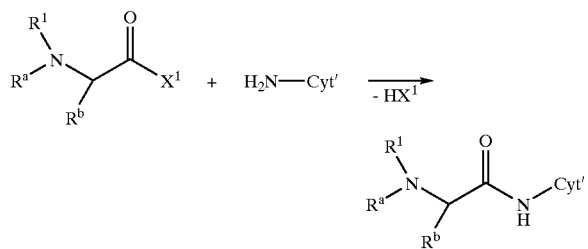

If a linker residue (L) is required between the oligomeric part and the cytotoxic or cytostatic agent the block synthesis can be done in the same manner.

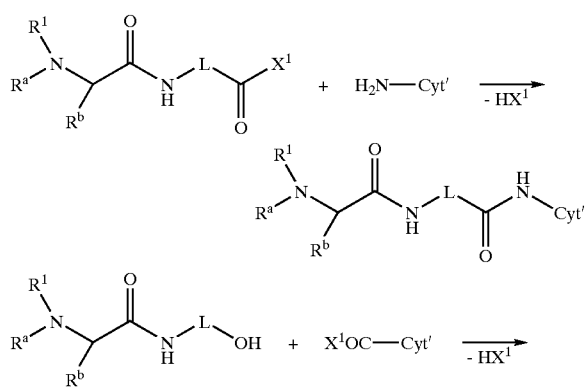

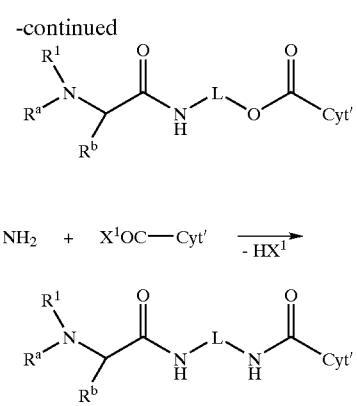

If the cytotoxic or cytostatic bears a carboxy function for the attachment to the oligomeric part, the linker molecule can be an imine or an amino alcohol and the block synthesis of such compounds can be carried out in a similar way by reaction of the activated XOC—Cyt' with either the hydroxy or the amino component.

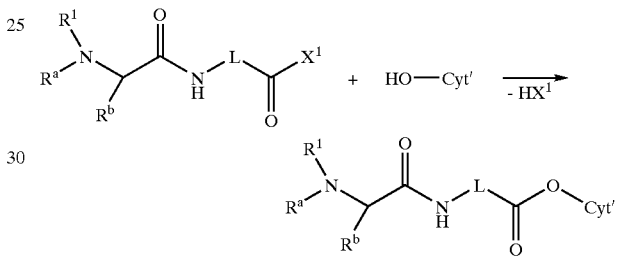

If the cytotoxic or cytostatic reagent has a hydroxy function which is suitable for the coupling to the oligomeric part the linker residue may be an amino carboxylic acid and a block synthesis can be done similarly.

If necessary, other functional groups in the units Cyt', L, hydroxyproline, A, B and D which shall not react during the assembly of the target molecules may be protected by suitable protecting groups. Suitable protecting groups are well known from the state of the art (P. G. M. Wuts, "Protective groups in organic synthesis", John Wiley and Sons Inc., New York 1991). These protecting groups are removed at the end of the synthesis.

By way of example only, useful amino-protecting groups may include, for example, C$_1$–C$_{10}$ alkanoyl groups such as formyl, acetyl dichloroacetyl, propionyl, 3,3diethylhexanoyl, and the like, C$_1$–C$_{10}$ alkoxycarbonyl and C$_6$–C$_{17}$ aralkyloxycarbonyl groups such as tert-butoxycarbonyl, benzyloxycarbonyl (BOC), fluorenylmethoxycarbonyl, and the like. Most preferred is fluorenylmethoxycarbonyl (FMOC).

Suitable carboxy-protecting groups may include, for example, C$_1$–C$_{10}$ alkyl groups such as methyl, tert-butyl, decyl; C$_6$–C$_{17}$ aralkyl such as benzyl, 4-methoxybenzyl, diphenylmethyl, triphenylmethyl, fluorenyl; tri-(C$_1$–C$_{10}$ alkyl)silyl or (C$_1$–C$_{10}$ alkyl)-diarylsilyl such as trimethylsilyl, dimethyl-tert-butylsilyl, diphenyl-tert-butylsilyl and related groups.

To achieve such ester- or amide formations, it may be necessary to activate the carbonyl group of the Larboxylic acid for a nucleophilic attack of an amine or alcohol, i.e. X to be an activation group or leaving group which is suitable to be substituted by an amino group. This activation can be done by conversion of the carboxylic acid into an acid chloride or acid fluoride or by conversion of the carboxylic acid into an activated ester, for instance a N-hydroxysuccinimidyl ester or a pentafluorophenyl ester. Another method of activation is the transformation into a symmetrical or unsymmetrical anhydride. Alternatively, the formation of the amide- or ester bonds can be achieved by the use of in situ coupling reagents like benzotriazole-1-yl-oxy-tris-pyrrolidino-phosphonium hexafluorophosphate (PyBOP) (E. Frerot et al., *Tetrahedron*, 1991, 47, 259–70), 1,1'-carbonyldimidazole (CDI) (K. Akaji et al., *THL*, 35, 1994, 3315–18), 2-(1H-benzotriazole-1-yl)-1,1,3,3-tetramethyluronium tetrafluoroborate (TBTU) (R. Knorr et al., *THL*, 30, 1989, 1927–30), 1-(mesitylene-2-sulonyl)-3-nitro-1H-1,2,4-triazole (MSNT) (B. Blankenmeyer-Menge et al., *THL*, 31, 1990, 1701–04).

As an alternative to the block synthesis the molecules in the general formula (I) can be assembled in a step by step manner starting at the right hand side by stepwise condensation reactions of the respective monomers Cyt', L, the cyclic amino acid group formed by $R^a$, $R^b$ and the interjacent N—C group, in particular proline or hydroxyproline, A, B and D. For the condensation reaction the same above mentioned coupling methods can be applied. to Since the units L, proline/hydroxyproline, A, B and D are at least bifunctional molecules containing an amino- and (at least the units A, B, D, and the cyclic amino acid group formed by Ra, Rb and the interhjacent N—C group, in particular proline/hydroxyproline) a carboxy group, the amino group needs to be blocked by a protecting group (PG) prior to the activation of the carboxylic function. For the protection of the amino groups the group BOC or preferably the group FMOC can be applied. After the coupling reaction the amino protecting group has to be removed and the coupling with the next Fmoc- or Boc-protected unit can be carried out. If necessary, other functional groups in the units Cyt', L, the cyclic amino acid group formed by $R^a$, $R^b$ and the interhjacent N—C group, in particular hydroxyproline, A, B and D which shall not react during the assembly of the target molecules may be protected by suitable protecting groups. These protecting groups are removed at the end of the synthesis.

Capping groups as defined in the context of formula (I) may also serve as protection groups, in particular when the last (N-terminal) amino carboxylic acid unit is added. In this latter case the protecting group is not removed as it is a part of the target molecule. Alternatively, the capping group may be added after the last amino carboxylic acid unit has been coupled and deprotected.

The step by step synthesis is outlined in the following schemes. The second scheme is exemplary as the linker residue as well as the Cyt' residue may contain other functional groups as indicated in this scheme (see above):

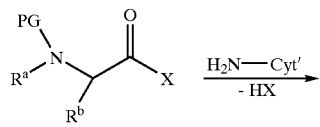

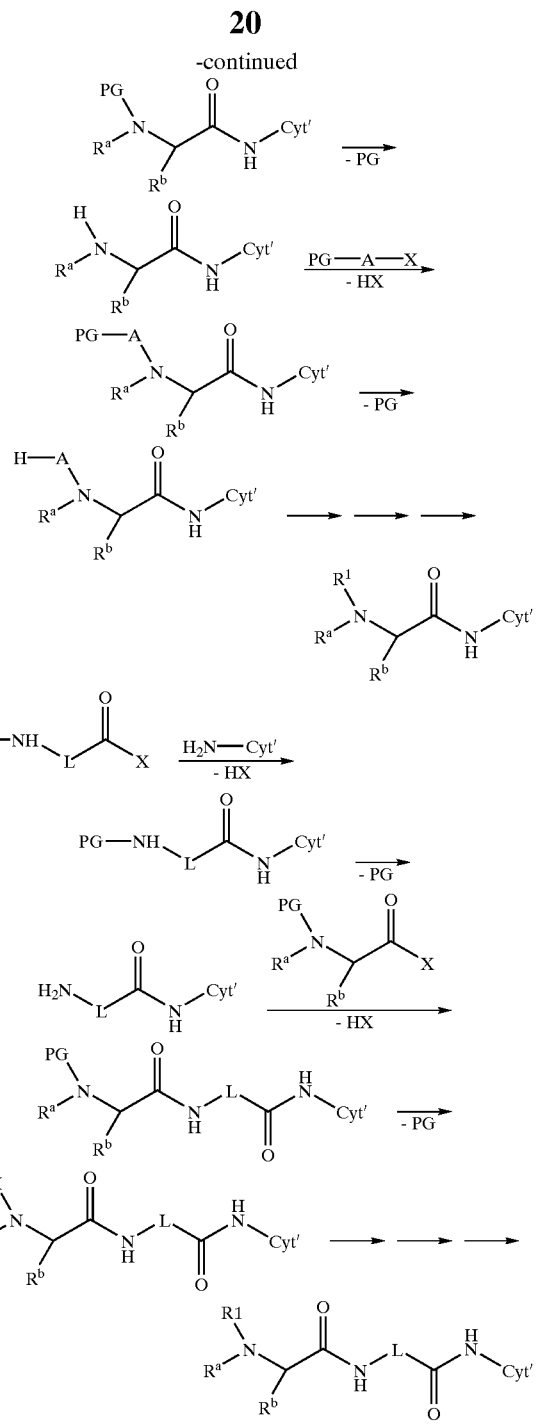

Accordingly, a further aspect of the invention is a process for the production of a compound of formula (I), characterised in that a compound of the general formula (V)

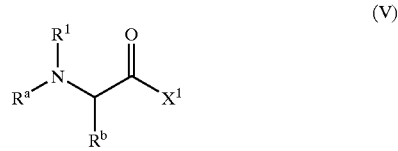

wherein R¹, Rᵃ and Rᵇ are as defined hereinabove, X¹ represents OH, or a leaving group which is suitable to be substituted by a amino group,
is reacted with a compound HN(R⁴)—Cyt', wherein Cyt' is the residue of a cytotoxic or cytostatic compound, and R⁴ is as defined hereinabove.

Preferably, X¹ within formula (V) is a leaving group, for example —Cl, —F, N-hydroxysuccinimidyl, pentafluorophenyl, or a carboxylate. Alternatively, X¹ may be OH, and condensation is achieved by the use of an in situ coupling reagent, for example benzotriazole-1-yl-oxy-tris-pyrrolidino-phosphonium hexafluorophosphate (PyBOP), 1,1'-carbonyldimidazole (CDI), 2-(1H-benzotriazole-1-yl)-1,1,3,3-tetramethyluronium tetrafluoroborate (TBTU), or 1-(mesitylene-2-sulfonyl)-3-nitro-1H-1,2,4-triazole (MSNT).

A further aspect of the invention is a process for the production of a compound of formula (I), characterised in that a compound of the general formula (VI)

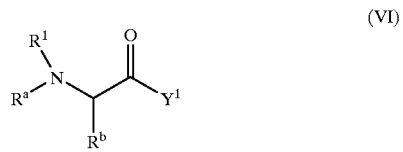

(VI)

wherein R¹, Rᵃ and Rᵇ are as defined in claim 1, Y¹ represents L—COX², wherein L is a linker residue, and X² represents OH, or a leaving group which is suitable to be substituted by a amino group or a hydroxy group,
is reacted with a compound H₂N—Cyt' or with a compound HO—Cyt', wherein Cyt' is the residue of a cytotoxic or cytostatic compound.

Preferably, X² within formula (VI) is a leaving group, for example —Cl, —F, N-hydroxysuccinimidyl, pentafluorophenyl, or a carboxylate. Alternatively, X² may be OH and condensation is achieved by the use of an in situ coupling reagent, for example benzotriazole-1-yl-oxy-tris-pyrrolidino-phosphonium hexafluorophosphate (PyBOP), 1,1'-carbonyldimidazole (CDI), 2-(1H-benzotriazole-1-yl)-1,1,3,3-tetramethyluronium tetrafluoroborate (TBTU), or 1-(mesitylene-2-sulfonyl)-3-nitro-1H-1,2,4-triazole (MSNT).

A further aspect of the invention is a process for the production of a compound of formula (I), characterised in that a compound of the general formula (VII)

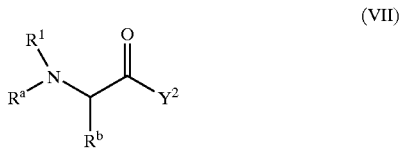

(VII)

wherein R¹, Rᵃ and Rᵇ are as defined hereinabove, Y² is of formula L—OH or L—NH₂,
wherein L is a linker residue,
is reacted with a compound X³OC—Cyt', wherein X³ may be OH, or a leaving group which is suitable-to be substituted by a amino group or a hydroxy group, and wherein Cyt' is the residue of a-cytotoxic or cytostatic compound.

Preferably, X³ of the compound X³OC—Cyt' is a leaving group, for example —Cl, —F, N-hydroxysuccinimidyl, pentafluorophenyl, or a carboxylate. Alternatively, X may be OH and condensation is achieved by the use of an in situ coupling reagent, for example benzotriazole-1-yl-oxy-tris-pyrrolidino-phosphonium hexafluorophosphate (PyBOP), 1,1'-carbonyldimidazole (CDI), 2-(1H-benzotriazole-1-yl)-1,1,3,3-tetramethyluronium tetrafluoroborate (TBTU), or 1-(mesitylene-2-sulfonyl)-3-nitro-1H-1,2,4-triazole (MSNT).

A further aspect of the invention is a process for the production of a compound of formula (I), characterised in that a compound H₂N—Cyt' is condensed stepwise with the units making up the compound of formula (I). Before each coupling step, it may be necessary to remove a protecting group PG, if present.

Accordingly, a further aspect of the invention is a process for the production of a compound of formula (I), characterised in that a compound of the general formula (VIII)

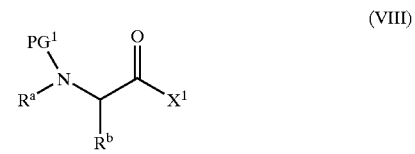

(VIII)

wherein PG¹ is a protecting group, and the other the substituents have the meaning as described before,
is reacted with a compound HN(R⁴)—Cyt', wherein Cyt' is the residue of a cytotoxic or cytostatic compound;
the protecting group PG¹ is then removed and the resulting compound of formula (VIIIA)

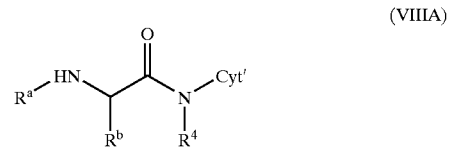

(VIIIA)

is subsequently reacted with a compound PG²—A—X⁴, wherein
PG² is a protecting group, and X⁴ represents OH, or a leaving group suitable to be substituted by a amino group;
and further coupling steps are carried out, if necessary, until the complete compound is obtained.

PG¹ and pG² may be, for example BOC, or preferably FMOC.

Accordingly, a further aspect of the invention is a process for the production of a compound of formula (I), characterised in that a compound of formula PG³—N(R⁴)—L—COX³, wherein
PG3 is a protecting group, and the other substituents have the meaning as described before, is reacted with a compound of formula Y⁴—Cyt', wherein
Cyt' is the residue of a cytotoxic or cytostatic compound; and Y⁴ represents H₂N or HO; the protecting group PG³ is then removed; and the resulting compound HN(R⁴)—L—Y⁴—Cyt' is reacted with a compound of formula (VIII)

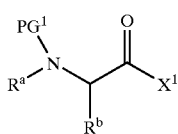

the protecting group PG$^1$ is then removed and the resulting compound of formula

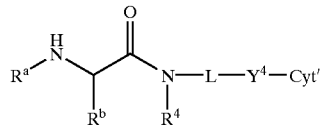

is then reacted with a compound PG$^4$—A—X$^4$, wherein
PG$^4$ is a protection group, and X$^4$ may be OH, or a leaving group suitable to be substituted by a amino group;
and further coupling steps are carried out, if necessary, until the complete molecule is obtained.

A further aspect of the invention is a process for the production of a compound of formula (I), characterised in that
a compound of formula PG$^5$—N(R$^4$)—L—Y$^5$, wherein
PG$^5$ represents a protecting group, Y$^5$ represents OH or NH$_2$ and the substituents have the meaning as described before,
is reacted with a compound of formula X$^5$OC—Cyt', wherein
Cyt' is the residue of a cytotoxic or cytostatic compound and X$^5$ is OH or a suitable leaving group;
the protecting group PG$^5$ is then removed; and the resulting compound HN(R$^4$)—L—Y$^5$—CO—Cyt' is reacted with a compound of formula (VIII)

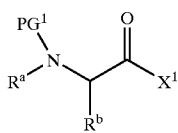

the protecting group is then removed and the resulting compound

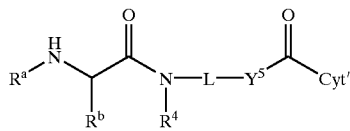

is then reacted with a compound PG$^2$—A—X$^4$, wherein
PG$^2$ is a protecting group, and X$^4$ represents OH, or a leaving group suitable to be substituted by a amino group;
and further coupling steps are carried out, if necessary, until complete molecule is obtained.

Another aspect of the present invention are the novel intermediate compounds of formula VIIIA

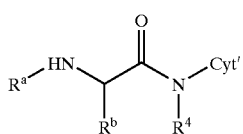

wherein R$^a$, R$^b$, R$^4$ and Cyt' are as defined hereinabove.

The compounds of the invention are intended for medical use. In particular, these compounds are useful for the treatment of tumours which are associated with stromal fibroblasts that express FAPα and which are generally not optimally treated with available cytotoxic and/or cytostatic agents. Tumours with this property are, for example, epithelial cancers, such as lung, breast, and colon carcinomas. Tumours, such as bone and soft tissue sarcomas which express FAPα, may also be treated with these compounds.

Consequently, another aspect of the present invention are pharmaceutical compositions comprising a compound of the present invention and optionally one or more suitable and pharmaceutically acceptable excipients, as exemplified in: *Remington: the science and practice of pharmacy*. 19th ed. Easton: Mack Publ., 1995. The pharmaceutical compositions may be formulated as solids or solutions. Solid formulations may be for preparation of a solution before injection. Preferably, the pharmaceutical compositions of the invention are solutions for injection. They may be administered systemically, e.g. by intravenous injection, or topically, e.g. by direct injection into the tumour site. The dosage will be adjusted according to factors like body weight and health status of the patient, nature of the underlying disease, therapeutic window of the compound to be applied, solubility, and the like. It is within the knowledge of the expert to adjust dosage appropriately. For doxorubicin conjugates, for example, the dose will preferably be in the range from 10 mg/m$^2$ to 1350 mg/m$^2$, but also higher or lower doses may be appropriate.

Accordingly, a further aspect of the present invention is the use of a compound of the invention in the preparation of a pharmaceutical composition for the treatment of cancer. Furthermore, an aspect of the invention is a method of treatment of cancer, comprising administering an effective amount of a pharmaceutical composition of the invention to a patient. Indications include the treatment of cancer, specifically, 1) The treatment of epithelial carcinomas including breast, lung, colorectal, head and neck, pancreatic, ovarian, bladder, gastric, skin, endometrial, ovarian, testicular, esophageal, prostatic and renal origin;
2) Bone and soft-tissue sarcomas: Osteosarcoma, chondrosarcoma, fibrosarcoma, malignant fibrous histiocytoma (MFH), leiomyosarcoma;
3) Hematopoietic malignancies: Hodgkin's and non-Hodgkin's lymphomas;
4) Neuroectodermal tumors: Peripheral nerve tumors, astrocytomas, melanomas;
5) Mesotheliomas.

Also included are the treatment of chronic inflammatory conditions such as rheumatoid arthritis, osteoarthritis, liver cirrhosis, lung fibrosis, arteriosclerosis, and abnormal wound healing.

A further aspect of the invention is a method of treatment of cancer, wherein a prodrug is administered to a patient wherein said prodrug is capable of being converted into a cytotoxic or cytostatic drug by an enzymatic activity, said enzymatic activity being the expression product of cells associated with tunour tissue. Preferably, said enzymatic activity is the proteolytic activity of FAPα.

One method of administration of the compounds is intravenous infusion. Other possible routes of administration include intraperitoneal (either as a bolus or infusion), intramuscular or intratumoral injection. Where appropriate, direct application may also be possible (for example, lung fibrosis).

FIGURES

FIG. 1: Cleavage of doxorubicin-peptide conjugates by FAPα. Chromatograms for ZGP-Dox (Z-Gly-(L)-Pro-Doxorubicin) after incubation with purified FAPmCD8 fusion protein (A), or with buffer (B). See example 5.

Figure 2:
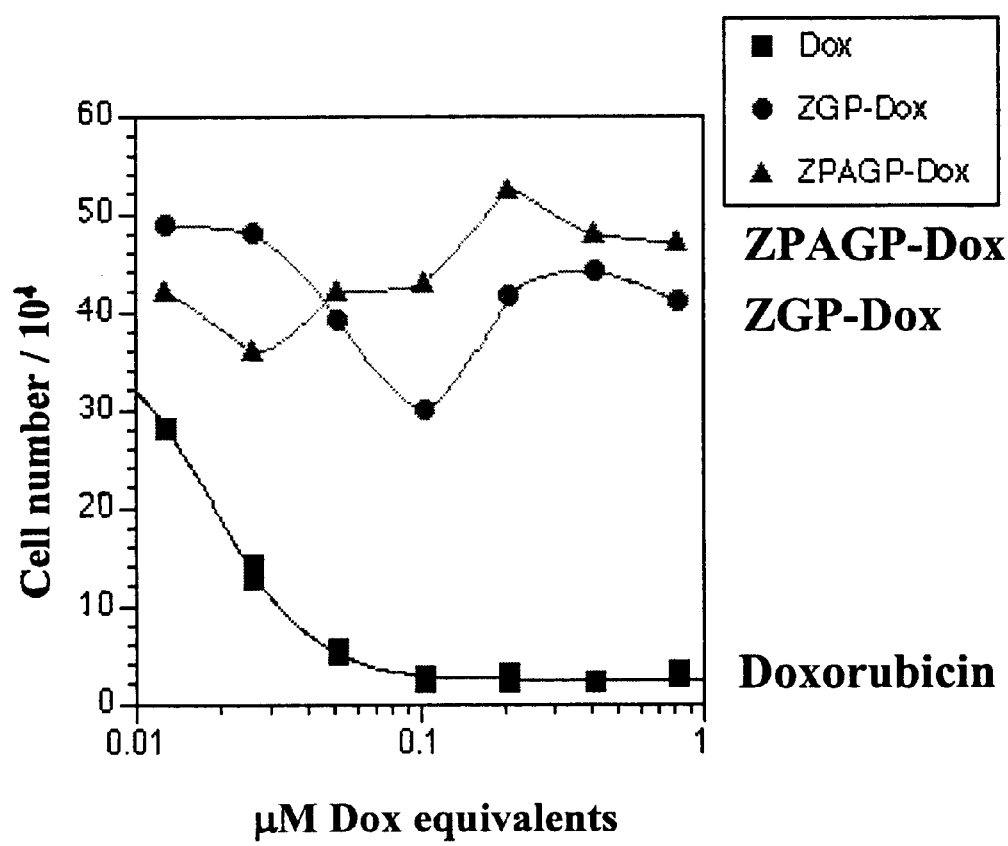

FIG. 2: Reduction of doxorubicin cytotoxicity by conjugation of doxorubicin to FAPα-cleavable peptides. See example 6.

Figure 3:
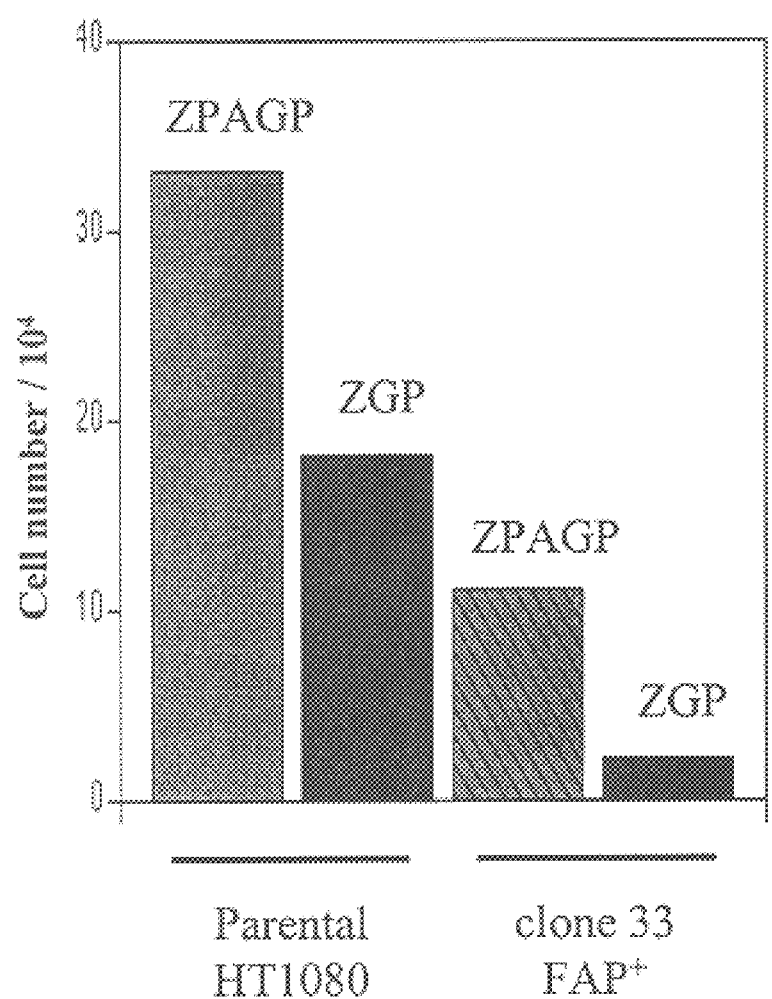

FIG. 3: Demonstration of cytotoxicity of doxorubicin released from FAPα-cleavable doxorubicin-peptide conjugates by FAPα-expressing HT1080 clone 33 cells versus parental HT1080 cells. See example 8.

Figure 4:
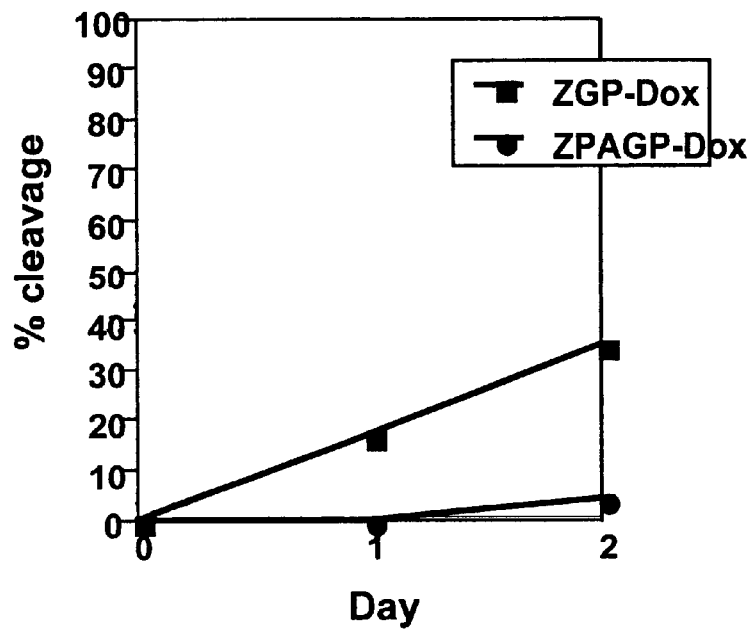
Figure 4:
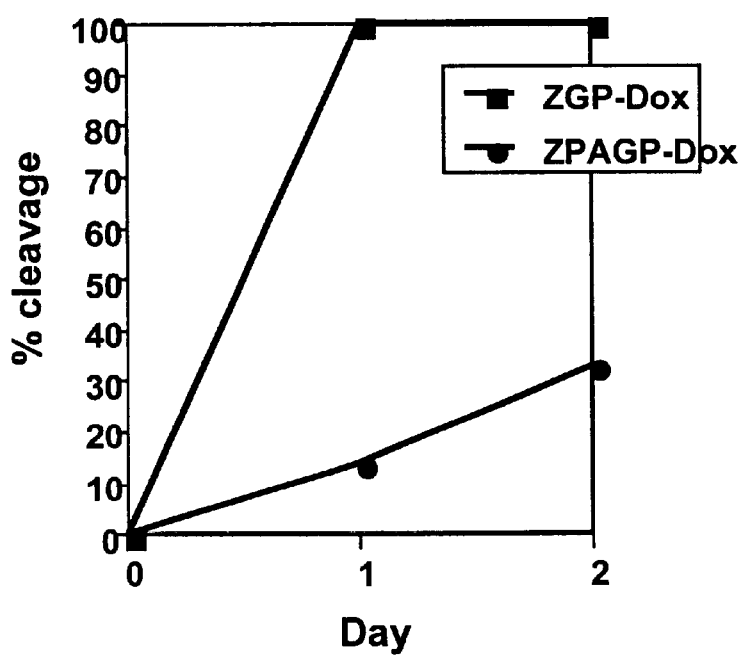

FIG. 4: Plasma stability of N-Cbz-Gly-(L)-Pro-Doxorubicin and N-Cbz-(L)-Pro-(L)-Ala-Gly-(L)-Pro-Doxorubicin in mouse and human plasma. See example 9.

Figure 5:
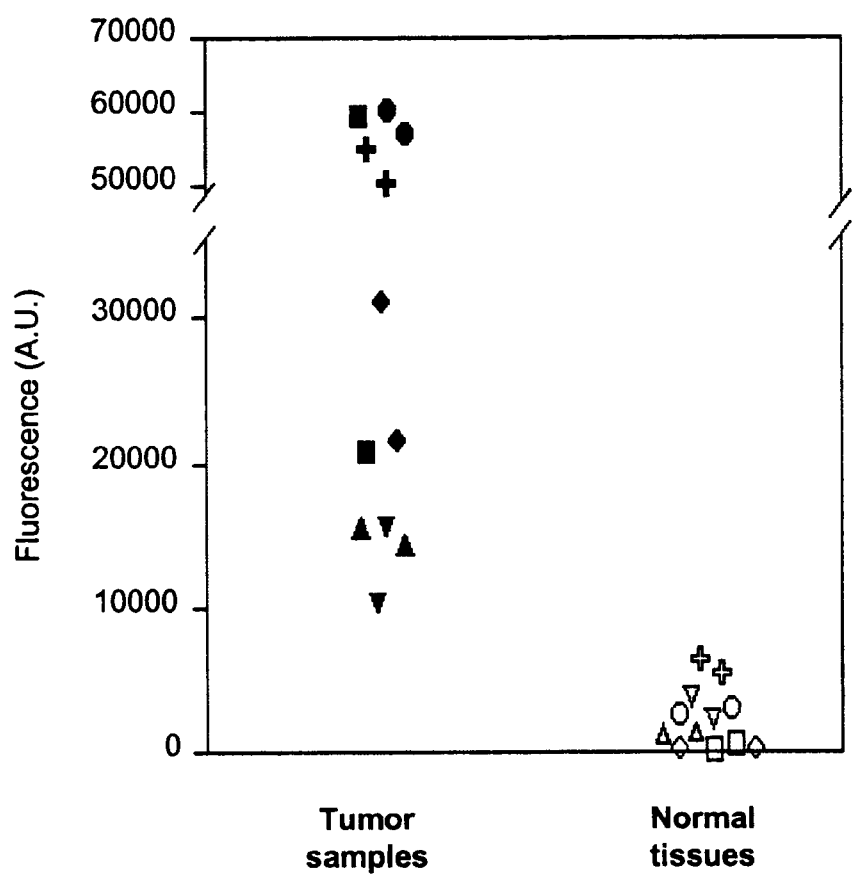

FIG. 5: Demonstration of FAPα enzyme activity and confirmation of its apparent molecular weight in human tumour tissue samples. See Example 12.

One skilled in the art will appreciate that although specific reagents and reaction conditions are outlined in the following examples, modifications can be made which are meant to be encompassed by the scope of the invention. The following examples, therefore, are intended to further illustrate the invention and are not limiting.

EXAMPLES

Example 1

Synthetic Procedures of Doxorubicin Conjugates

N-Cbz-Gly-Pro-Doxorubicin: N-Cbz-Gly-Pro (116.1 mg, 0.37mmol) and N-hydroxy succinimide (44 mg, 0.37 mmol) were weighed out and placed in a 2 neck-round bottom flask under dinitrogen. Anhydrous N,N-dimethylformamide (20 ml) was added and the flask was cooled to 0° C. in an ice bath. Dicyclohexylcarbodiimide (78 mg, 0.37 mmol) was added as a 1 ml solution in N,N-dimethylforrnamide. The solution was stirred at 0° C. for 40 minutes.

Doxorubicin.HCl (100 mg, mmol) was weighed into a vial with a small stir bar and placed under dinitrogen. N,N-Dimethylformamide (3 ml) and N,N-diisopropylethylamine (33.1 µl 0.19 mmol) were added to the vial with stirring. The doxorubicin solution was added via syringe to the peptide solution, and the vial was rinsed with an additional 2 ml of N,N-dimethylformamide. The ice bath was removed and reaction mixture was stirred for approximately 48 hours at room temperature.

The reaction solution was extracted with ethyl acetate (500 ml). The ethyl acetate was washed with of 10% aqueous citric acid solution (250 ml), saturated aqueous sodium bicarbonate (250 ml) and brine (250 ml) sequentially. The organic extract was dried with anhydrous $MgSO_4$, and the solvent was removed with a roto-evaporator. The product, which was rich in DMF contaminant, was chromatographed on a C-18 reversed phase flash column with 8:2 methanol:water as the eluent. One orange spot, rf≈0.3, which fluoresced under long wave UV light was isolated. The methanol was removed with the roto-evaporator and the last traces of solvent were removed with the high vacuum pump overnight.

N-Cbz-Pro-Ala-Gly-Pro: N-Cbz-Pro-Ala (5 g, 15 mmol) and carbonyldiimidazole (2.43 g, 15 mmol) were placed in a 250 ml, 3-neck round bottom flask under an argon atmosphere. Anhydrous tetrahydrofuran (50 ml) was added and the solution was stirred at room temperature for approximately 45 minutes. Rigorous evolution of a gas ($CO_2$) was observed.

Into a separate flask was weighed Gly-Pro-OCH$_3$.HCl (2.9 g, 15 mmol). Tetrahydrofuran (5 ml) and N,N-diisopropylethylamine (5.23 ml, 30 mmol) were added and the solution was stirred for several minutes. The material that dissolved was added via syringe to the activated peptide, the remaining material was dissolved in a minimum amount of $CH_2Cl_2$ and also added to the activated peptide via syringe.

The reaction solution was stirred overnight at room temperature (15 hours) and in the morning there was copious amounts of white precipitate. The reaction mixture was washed with 10% aqueous citric acid solution (300 ml) and extracted with ethyl acetate (500 ml). The ethyl acetate extract was washed with saturated aqueous bicarbonate solution (300 ml) and dried with brine (300 ml) and anhydrous $MgSO_4$ The ethyl acetate was removed with the roto-evaporator to yield 5 g of a colourless oil, which gave satisfactory characterisation data.

The crude oil of the N-Cbz-Pro-Ala-Gly-Pro-OCH$_3$ (5g, 12 mmol) was dissolved in methanol (20 ml) in a round bottom flask. The flask was placed in an ambient temperature water bath. 1 N Sodium hydroxide solution (12 ml) was added cautiously. The solution was stirred for 3.5 hours after which time 1 N HCl solution (12 ml) was added. The solution was concentrated on the roto-evaporator and a few more drops of 1 N HCl was added until the pH is approximately 1.5 with pH paper. The water was removed with the vacuum pump to give an oil, which was recrystalized slowly from ethanol.

N-Cbz-Pro-Ala-Gly-Pro-Doxorubicin: N-Cbz-Pro-Ala-Gly-Pro (180 mg, 0.38 mmol) was dissolved in anhydrous N,N-dimethylformamide (15 ml). 1-Hydroxybenzotriazole (51.3 mg, 38 mmol) and dicyclohexylcarbodiimide (78 mg, 38 mmol) were dissolved in 1 ml each of N,N-dimethylformamide and added to the peptide as solutions. The reaction mixture was stirred at room temperature for 45 minutes.

Doxorubicin.HCl (116 mg, 20 mmol) was weighed into a separate vial and dissolved in N,N-dimethylforrnamide (3 ml). N,N-Diisopropylethylamine (34.8 µl, 20 mmol) was syringed into the vial containing the doxorubicin, and the contents were stirred for several minutes to ensure complete dissolution. The doxorubicin solution was added via syringe to the activated peptide. The solution was stirred for 48 hours at room temperature.

The product was extracted with ethyl acetate (2 l) and washed with 10% aqueous citric acid solution (500 ml). The ethyl acetate layer was separated, dried with $MgSO_4$ and concentrated to an oil on the roto-evaporator. The oil was chromatographed on C-18 reversed phase silica gel, which gave an orange, long wave UV fluorescing spot at rf=0.25. The final product gave satisfactory characterization data.

Example 2

Preparation of FAPα-expressing Cell Lines

Mammalian cell lines expressing recombinant FAPα were prepared. HT1080 fibrosarcoma cells, widely known and available from the DSMZ (German Collection of Microorganisms and Cell Cultures, Braunschweig, Germany) under the accession number DSMZ ACC 315, were maintained in a DMEM/F12 mix 50:50 containing 10% fetal bovine serum in an atmosphere of 95% air and 5% $CO_2$. HT1080 cells were transfected with FAP.38 vector (WO 97/34927, Scanlan et al., loc. cit.) using the Lipofectin method according to the manufacturer's instructions (Gibco/BRL). Transfectants were selected for resistance to antibiotics (200 µg/ml Geneticin) and thereafter maintained in medium containing Geneticin. Individual colonies of resistant cells were picked, grown to confluence in 10 cm tissue culture petri dishes and tested for FAPα expression in an immunofluorescence assay using the FAPα-specific monoclonal antibody F19, as described (Garin-Chesa et al. (1990) *Proc. Natl. Acad. Sci. USA* 87(18), 7235–7239). The parental HT1080 cell line showed no detectable FAPα expression in this immunofluorescence assay, while one clone, referred to hereafter as HT1080 clone 33, was positive for FAPα.

Similarly, human embryonic kidney 293 cells, widely known and available from American Tissue Type Collection (Rockville, Md.), were maintained in a DMEM containing 10% fetal bovine serum in an atmosphere of 95% air and 5% $CO_2$. Cells were transfected with a FAPα expression vector, pFAP.38 using calcium phosphate transfection as described (Park, J. E., Chen, H. H., Winer, J., Houck, K. A. & Ferrara, N. (1994). Placenta growth factor. Potentiation of vascular endothelial growth factor bioactivity, in vitro and in vivo, and high affinity binding to Flt-1 but not to Flk-1/KDR. *J. Biol. Chem.* 269(41), 25646–5654). Transfectants were selected and analyzed as described above for FAPα expresion. The parental 293 cell line showed no detectable FAPα expression. One clone, referred to hereafter as 293-I/2, was FAPα positive.

Example 3

Examination of FAPα Expression in Transfected Cell Lines

FAPα expression was examined in the HT1080 and HT1080 clone 33 cells. Metabolic labeling, immunoprecipitations and fluorography were performed essentially as described (Park et al. (1991) *Somatic Cell Mol. Genet.* 17(2), 137–150). HT1080 and HT1080 clone 33 cells were metabolically labelled with $^{35}S$-methionine. Detergent extracts of these cells were immunoprecipitated with monoclonal antibody F19 or with mouse IgG1 antibody as a negative control. Precipitates were boiled in sample buffer and separated by sodium dodecyl sulfate gel electrophoresis (as described by Laemmli (1970) *Nature* 227(259), 680–685). Fluorographic analysis of the resulting gel confirmed that the HT1080 clone 33 cells produce FAPα protein. No FAPα protein was detectable in extracts of the parental HT1080 cells nor in immunoprecipitates with mouse IgG1.

Example 4

Soluble Recombinant FAPα

A soluble recombinant form of FAPα protein was prepared as follows. A cDNA encoding the extracellular domain (ECD) of murine CD8α (Genbank M12825), consisting of the N-terminal 189 amino acids of CD8α, was ligated to a cDNA encoding the extracellular domain of FAPα (amino acids 27 to 760), generating a fusion protein construct, FAPmCD8, similar in structure to the CD8α-CD40 ligand fusion protein, as previously described (Lane et al. (1993) *J. Exp. Med.* 177(4), 1209–1213). The cDNAs were verified by sequencing and inserted into the pVL1393 vector. Transfection of Sf9 cells and amplification of the resulting recombinant baculovirus were performed as described (O'Reilly (1994) *Baculovirus Expression Vectors: A Laboratory Manual*, Oxford University Press, New York). The culture supernatant of High Five cells infected with recombinant FAPmCD8 baculovirus for four days was collected and cleared by ultracentrifugation. FAPmCD8 fusion protein was purified from such supernatants using an anti-FAPα monoclonal antibody immobilized on activated agarose beads (Pierce Chemical, Indianapolis, Ind., USA). The culture supernatant was passed through the antibody affinity column and eluted by pH shift using 0.1 M citrate buffer, pH 3. The samples were immediately neutralized with a saturated Tris solution (Sigma Chemicals, St. Louis, Mo.) and protein-containing fractions were pooled.

Example 5

Measurement of Cleavage of Doxorubicin-peptide Conjugates

Samples were separated by reversed-phase high performance liquid chromatographic (HPLC) assay that was established to measure cleavage of doxorubicin-peptide conjugates. The HPLC system consisted of a Waters 717 autosampler equipped with a 100 microliter (µl) loop and two Waters model 510 pumps to deliver solvents. Separations were performed under isocratic conditions at a flow rate of 0.7 ml/min on a Nucleosil C-18 column, 100 mm long×4 mm I.D. with 5 µm particle size (Dr. Ing. H. Knauer GmbH, Berlin). The mobile phase consisted of methanol-:water (70:30, v/v) containing 0.2 M ammonium acetate, adjusted to pH 3.2. Free doxorubicin and doxorubicin-peptide conjugates were detected by fluorescence (excitation, 475 nm; emission, 585 nm) using a Waters 474 fluorescence detector. Injection, solvent delivery, data acquisition, and data analysis were all performed using the Millennium 2010 chromatography software package (Waters Corp., Milford, Mass., USA). Substances to be tested were first dissolved in dimethyl sulfoxide at a concentration of 5 mM and subsequently diluted in aqueous solution before being applied to the HPLC column.

The ability of soluble recombinant FAPα enzyme to release free doxorubicin from doxorubicin-peptide conjugates was examined. Doxorubicin-peptide conjugate stock solutions (5 mM) were diluted with Hepes-buffered saline pH 7.4 to a final concentration of 50 to 100 µM. Twenty µl of the resulting solution was mixed with 50 µl of purified FAPmCD8 fusion protein (approximately 20 ng) described above and 30 µl Hepes-buffered saline, pH 7.4. The mixture was allowed to incubate at 37° C. for 1 day and release of free doxorubicin was measured in the HPLC assay described. Areas under each peak were quantified using the software package above and the initial value was set to 100%. The rate of release of free doxorubicin was measured by the appearance of a peak with the same retention time as free doxorubicin under these HPLC conditions. The areas under each peak were used to calculate the relative amounts of free doxorubicin to doxorubicin-peptide conjugate. Integration of peak areas to determine percent cleavage was carried out using the Millennium 2010 chromatography software package above. As seen in the chromatograms for ZGP-Dox (N-Cbz-Gly-Pro-Doxorubicin) shown in FIG. 1, the doxorubicin-peptide conjugate could be converted to free doxorubicin after incubation with purified FAPmCD8 fusion protein but the retention time of the conjugate was not altered by incubation with buffer.

Example 6

Reduction of Cytotoxicity of Doxorubicin by Conjugation to FAPα-cleavable Peptides The ability of FAPα-cleavable peptides to block the cytotoxic action of doxorubicin on FAPα-negative, doxorubicin-sensitive cells was determined. K562 cells, available from American Type Tissue Culture Collection, Rockville, Md., USA (ATCC Number: CCL-243), were seeded in 96 well plates (Greiner Scientific) at a density of 1000 cells/well. Serum-free cell culture media containing various concentrations of free doxorubicin or equivalent molar concentrations of doxorubicin-peptide conjugates were added to the cells. Four days later, cell number was determined using an automated CASY™ cell counter (Scharfe System GmbH, Reutlingen, Germany). The results are shown in FIG. 2.

Example 7

Release of Free Doxorubicin by Cell-bound FAPα

The ability of cell-bound FAPα enzyme to release free doxorubicin from doxorubicin-peptide conjugates was examined. Each conjugate was dissolved in serum-free cell culture medium at a final concentration of 1 µM. Ten milliliters of this solution was added to confluent monolayers of HT1080 or HT1080 clone 33 cells in 10 cm tissue culture dishes for 19 hours at 37° C. The media were removed and release of doxorubicin measured as described in Example 5. The FAP-expressing cell line, HT1080 clone 33, converted 81% and 43% of the ZGP-Dox (N-Cbz-Gly-Pro-Doxorubicin) and ZPAGP-Dox (N-Cbz-Pro-Ala-Gly-Pro-Doxorubicin) conjugates to free doxorubicin, respectively. The parental HT1080 cell line converted only 9% of ZGP-Dox to free doxorubicin under the same conditions. Little or no detectable conversion of ZPAGP-Dox to free doxorubicin by the parental HT1080 cell line was observed under these conditions.

Example 8

Killing of Sensitive Cells by FAPα-released Doxorubicin

The ability of FAPα to generate free doxorubicin capable of killing doxorubicin-sensitive cells was determined. K562 cells, available from American Type Tissue Culture Collection, Rockville, Md., USA (ATCC Number: CCL-243), were seeded in 96 well plates (Greiner Scientific) at a density of 1000 cells/well. Serum-free cell culture media containing 1 µM doxorubicin-peptide conjugate was added to HT1080 or HT1080 clone 33 cells dishes for 19 hours at 37° C. The media were removed and release of doxorubicin was confirmed as in Example 5. Sixty-six µl of this medium was then added per well to the K562 cells. Four days later, cell number was determined using an automated CASY™ cell counter. The results are shown in FIG. 3.

Example 9

Plasma Stability of Doxorubicin-peptide Conjugates

The plasma stability of doxorubicin-peptide conjugates was measured using methods described in Example 5. Samples containing doxorubicin-peptide conjugates (at a concentration of 1 µM) were incubated in the presence of 10% (v/v) mouse or human plasma for the times indicated at 37° C. The results for ZGP-Dox and ZPAGP-Dox in mouse and human plasma are shown in FIG. 4.

Example 10

FAPα-catalyzed Cleavage of Selected 4-Methoxy-β-napthylamide-peptide Conjugates

To identify preferred FAPα peptide substrates, oligomers composed of natural and/or unnatural amino carboxylic acids were synthesized and coupled to Proline-4-methoxy-β-napthylamine (Pro-MNA) using methods known to the art (E. Wünsch, Synthese von Peptiden, in Methoden der organischen Chemie, Houben-Weyl (Eds. E. Müller, O. Bayer), Vol. XV, Part 1 and 2, Georg Thieme Verlag, Stuttgart, 1974).

Synthesis of Pro-Pro-4-methoxy-β-naphthylamide:

Boc-Pro (32 mg, 0.15 mmol), 2-(1H-benzotriazol-1-yl)-1,1,3,3-tetramethyluoronium tetrafluoroborate (53 mg, 0.15 mmol) and Pro-4-methoxy-β-naphthylamide hydrochloride (46 mg, 0.15 mmol) were dissolved in anhydrous N,N-dimethylformamide/tetrahydrofuiran 1:1 (4 ml). N-ethyldiisopropylamine (0.26 ml, 0.44 mmol) dissolved in N-methylpyrrolidone (1.7 molar) was added and the mixture was stirred at room temperature overnight.

The solvent was removed with a roto-evaporator and the residue was dissolved in ethyl acetate (10 ml) and extracted 3 times with water. The organic layer was dried with anhydrous $Na_2SO_4$ and the solvent was removed with a roto-evaporator. The residue was dissolved in trifluoroacetic acididichloromethane (1:4, 25 ml) and allowed to react for 1 hour. The solvent was removed with a roto-evaporator and the resulting oil was dried with a stream of nitrogen. The crude product was purified by preparative reversed phase HPLC applying a acetonitrile/water gradient. The product gave satisfactory analytical data (NMR and mass spectra).

Release of free MNA from the peptides was then measured in a Cytofluor fluorimeter (Per-Septive Biosystems, Inc.) using the 355 nm excitation/405 nm emission filter set. Enzyme kinetic parameters (Michaelis-Menten $K_m$ and $k_{cat}$ values) were calculated using methods known to the art (see for example, Yun, S. L. & Suelter, C. H. (1977). A simple method for calculating Km and V from a single enzyme reaction progress curve. *Biochim. Biophys. Acta* 480(1), 1–13.) with FAPα enzyme derived from membrane extracts of the 293-I/2 transfected cells in Example 2.

TABLE 1

$K_m$ and $k_{cat}$ values for FAPα-catalyzed cleavage of selected 4-methoxy-β-napthylamide (MNA)-peptide conjugates

| Substrates | $K_M$ [μM] | $K_{cat}$ [s$^{-1}$] | $K_{cat}/K_M \times 10^4$ [M$^{-1}$ s$^{-1}$] |
|---|---|---|---|
| Chg-Pro-MNA | 75 | 53.7 | 71.6 |
| Hyn-Pro-MNA | 69 | 27.4 | 39.7 |
| Pro-Pro-MNA | 154 | 49.5 | 32.1 |
| Val-Pro-MNA | 95 | 27.7 | 29.2 |
| Met-Pro-MNA | 127 | 27.9 | 22.0 |
| Arg-Pro-MNA | 278 | 50.6 | 18.2 |
| trans-Hyp-Pro-MNA | 254 | 37.9 | 14.9 |
| Gln-Pro-MNA | 273 | 40.5 | 14.8 |
| Ala-Pro-MNA | 267 | 35.7 | 13.4 |
| Lys-Pro-MNA | 530 | 57.1 | 10.8 |
| Ile-Pro-MNA | 43 | 12.6 | 8.8 |
| Met(O)-Pro-MNA | 378 | 26.9 | 7.1 |
| Ser-Pro-MNA | 872 | 28.3 | 3.3 |

Chg = cyclohexylglycine,
Hyn = 6-hydroxynorleucine,
trans-Hyp = trans-4-hydroxyproline Example 11

Specificity of MNA-coupled Peptides for FAPα Versus DPP-IV

Among the-known prolyl-specific serine oligopeptidase family members, the most closely related enzyme to FAPα is DPP-IV. Since active DPP-IV is found in plasma and on many different cell types, optimization of the relative (optional) selectivity of prodrug peptidics for FAPα compared to DPP-IV is necessary to reduce undesirable conversion of the prodrug at sites other than the tumor (e.g., in the plasma). To identify peptides specific for FAPα, cleavage of MNA-coupled peptides by FAPα was compared to the ability of DPP-IV to cleave the same peptide conjugates. Release of free MNA was measured as described in Example 9. Results are shown in Table 2.

TABLE 2

Comparison of cleavage selectivity of MNA-peptide conjugates by FAPα and DPP-IV.

| | Cleavage specificity | |
|---|---|---|
| | FAP | DPP IV |
| Ala-Pro-MNA | + | + |
| Z-Gly-Pro-MNA | + | − |
| Z-Pro-Ala-Gly-Pro-MNA | + | − |

+ indicates the enzyme was able to cleave the substrate
− indicates lack of cleavage Example 12

FAPα Activity in Tumour Samples

Enzyme activity of FAPα measured in human tumor samples. Ninety-six-well ELISA (enzyme-linked immunosorbent assay) plates (Costar, Corning, N.Y.) were coated overnight at 4° C. with 1 μg/ml F 19 antibody or control antibody in phosphate-buffered saline (PBS), pH 7.4. Wells were then rinsed with wash buffer (PBS, 0.1% Tween 20, pH 7.4) and excess binding sites were blocked with blocking buffer (5% bovine serum albumin in PBS, pH 7.4) for 1 hour at room temperature. FAPα activity was measured in tumor tissue (closed symbols) or matched normal control tissue (corresponding open symbols) from Concanavalin A-enriched membrane extracts (FIG. 5a). Tumor samples included breast (▲,■), colon (●), colon metastasized to the liver (▬), and lung cancer (▼,+). Extracts were added to F19-coated plates and incubated for 1 hour at room temperature. The unbound material was removed, wells were washed thrice with wash buffer, and FAPα enzyme activity was assayed using 100 μl Ala-Pro-AFC as described (WO 97/34927) for one hour at 37° C. The first two Concanavalin A fractions of each extract were measured and each value individually plotted. Background fluorescence (as measured using control antibody-coated plates) was subtracted from each value.

Independent biochemical confirmation of FAPα enzymatic activity and its apparent molecular mass in tumor extracts were obtained by labelling the aforementioned tissue extracts with $^{14}$C-labelled diisopropylfluorophosphate (DFP; NEN-DuPont, Cologne, Germany). DFP is known to bind covalently and irreversibly to active site serines of many serine proteases, thereby preventing further catalysis (Hayashi, R., Bai, Y. & Hata, T. (1975). Further confirmation of carboxypeptidase Y as a metal-free enzyme having a reactive serine residue. *J. Biochem.* 77(6), 1313–1318; Wahlby, S. & Engstrom, L. (1968). Studies on Streptomyces griseus protease. II. The amino acid sequence around the reactive serine residue of DFP-sensitive components with esterase activity. *Biochim. Biophys. Acta* 151(2), 402–408). $^{14}$C-DFP labelling of FAPα immunopurified from a tumor (T) corresponding to colon sample ● from FIG. 5a is shown in FIG. 5b. Sodium dodecyl sulfate polyacrylamide gel electrophoresis (Laemmli; U. K. (1970). Cleavage of structural proteins during the assembly of the head of bacteriophage T4. *Nature* 227(259), 680–685) and subsequent autoradiography (Park, J. E., Draper, R. K. & Brown, W. J. (1991). Biosynthesis of lysosomal enzymes in cells of the End3 complementation group conditionally defective in endosomal acidification. *Somatic Cell Mol. Genet.* 17(2), 137–150) of these samples revealed the presence of a labelled 95 kD protein, present in the colon cancer sample. No radiolabeled bands were observed in the normal matched control immunoprecipitate (N) nor with control antibody. The apparent molecular mass of the immunopurified, $^{14}$C-labelled protein seen in FIG. 5*b* agrees with previous reports for FAPα (Rettig, W. J., Su, S. L., Fortunato, S. R., Scanlan, M. J., Mohan Raj, B. K., Garin-Chesa, P., Healey, J. H. & Old, L. J. (1994). Fibroblast activation protein: Purification, epitope mapping and induction by growth factors. *Int. J. Cancer* 58(3), 385–392; WO 97/34927).

Example 13

Preparation of Protected Oligopepdides

Protected oligopeptides were either prepared in solution according to state-of-the-art protocols (e.g. M. Bodanszky and A. Bodanszky, "The practice of Peptide Synthesis", $2^{nd}$ edition, Springer, New York, 1994) or by solid phase synthesis on an Applied Biosystems model 430A automated peptide synthesizer. Deprotection and removal of the oligopeptide from the resin support were achieved by treatment with mixtures of trifluoracetic acid and frequently used scavenger additives. Purification was carried out by preparative high pressure liquid chromatography on reverse phase C18 silica columns using an aqueous 0.1% trifluoracetic acid/acetonitrile gradient. Identity and homogeneity of peptides were confirmed by high pressure liquid chromatography and mass spectral analysis. The oligopeptides that were prepared by this method are shown in Table 3.

TABLE 3

Oligopeptides.

Z—Gly—Pro—OH
Z—Pro—Ala—Gly—Pro—OH
Fmoc—Pro—Ala—Gly—Pro—OH
Fmoc—Chg—Pro—OH
Fmoc—Nle—Pro—OH
Fmoc—Hyn—Pro—OH
Fmoc—Pro—Pro—OH
Fmoc—Ser—Ala—Hyn—Pro—OH
Fmoc—Ser—Ala—Nle—Pro—OH
Fmoc—Ser—Ala—Chg—Pro—OH
Gly—Ser—Ala—Glu—Pro—OH
Gly—Gly—Ser—Ala—Glu—Pro—OH
Gly—Gly—Gly—Ser—Ala—Glu—Pro—OH
Ser—Glu—Asn—Arg—Lys—Val—Pro—OH
Gly—Tyr—Ser—Arg—Met—Pro—OH
Gln—Gly—Tyr—Ser—Arg—Met—Pro—OH
Gly—Gly—Gly—Trp—Pro—OH
Asn—Arg—Lys—Val—Pro—OH
Glu—Asn—Arg—Lys—Val—Pro—OH
Ser—Glu—Asn—Arg—Lys—Val—Pro—OH
Ala—His—Met—His—Pro—OH
Tyr—Ala—Phe—His—Pro—OH
Ser—Tyr—Ala—Phe—His—Pro—OH
Leu—Asn—Leu—Tyr—Met—Pro—OH
Gly—Ser—Ala—Glu—Pro—OH
Gly—Gly—Ser—Ala—Glu—Pro—OH
Gly—Gly—Gly—Ser—Ala—Glu—Pro—OH Z is benzyloxycarbonyl
Fmoc is 9-fluorenylmethoxycarbonyl
Chg is L-cyclohexylglycyl
Nle is L-norleucinyl
Hyn is L-6-hydroxynorleucinyl

Example 14

Preparation of Fmoc-Pro-Ala-Gly-Pro-Dox

Fmoc-Pro-Ala-Gly-Pro-OH (44 mg, 0.078 mmol) was dissolved in anhydrous N,N-dimethylformamide (10 ml) and pH was adjusted to 7.5 by N,N-diisopropylethylamine. N-hydroxysuccinimide (1 M in DMF, 78 μl, 0.078 mmol) was added and the mixture was cooled in an ice bath. Under stirring, dicyclohexylcarbodiimide (1 M in DMF, 87 μl, 0.087 mmol) was added and the solution was stirred at 0° C. for 1 h.

Doxorubicin*HCl (25 mg, 0.043 mmol) was dissolved in 20 ml anhydrous DMF and N,N-diisopropylethylamine (8.2 μl, 0.048 mmol) was added. This mixture was syringed to the activated peptide. The reaction was allowed to warm up to room temperature and was stirred for 48 h.

The solvent was then removed and the product was purified by preparative RP-HPLC on C18 using a gradient of water/acetonitrile with 0.1% trifluoracetic acid.

Analytical HPLC >90%; ES-MS 1110.5 (M+Na$^+$); 674.4

Example 15

Preparation of H-Pro-Ala-Gly-Pro-Dox

Fmoc-PAGP-Dox (prepared in Example 14, 44 mg, 0.040 mmol) was dissolved in THF/diethylamine (2:1, 20 ml) at 0° C. and stirred for 2 h. The solvent was removed and the product was purified by preparative RP-HPLC on C18 using a gradient of water/acetonitrile with 0.1% trifluoracetic acid.

Analytical HPLC >90%; ES-MS 866.6 [M+H]$^+$, 452.4

Example 16

Preparation of H-Chg-Pro-Dox

Fmoc-Chg-Pro-OH (46 mg, 0.096 mmol) was dissolved in anhydrous N,N-dimethylformamide (10 ml) and pH was adjusted to 7.5 by N,N-diisopropylethylamine. N-hydroxysuccinimide (1 M in DMF, 96 μl, 0.096 mmol) was added and the mixture was cooled in an ice bath. Under stirring, dicyclohexylcarbodiimide (1 M in DMF, 107 μl, 0.107 mmol) was added and the solution was stirred at 0° C. for 1 h.

Doxorubicin*HCl (31 mg, 0.053 mmol) was dissolved in 20 ml anhydrous DMF and N,N-diisopropylethyl amine (10 μl, 0.059 mmol) was added. This mixture was syringed to the activated peptide. The reaction was allowed to warm up to room temperature and was stirred for 48 h The solvent was then removed and the product was purified by preparative RP-HPLC on C18 using a gradient of water/acetonitrile with 0.1% trifluoracetic acid.

The lyophilized product was dissolved in THF/diethylamine (2:1, 20 ml) at 0° C. and stirred for 2 h. The solvent was removed and the product was purified by preparative RP-HPLC on C18 using a gradient of water/acetonitrile with 0.1% trifluoracetic acid.

Analytical HPLC >90%; ES-MS 780.2 (M+H+); 366.4

The following table shows the peptide-doxorubicin conjugates which have been prepared analogously and includes cleavage data by FAP (after 20 h).

TABLE 4

[Structure diagram]

| R$^1$ | Cleavage by FAP |
|---|---|
| Z-Gly- | >95% |
| Z-Pro-Ala-Gly- | >95% |
| Fmoc-Pro-Ala-Gly- | >95% |
| H-Pro-Ala-Gly- | ca. 11% |
| H-Chg- | >95% |
| H-Nle- | >95% |
| H-Hyn- | >95% |

Z is benzyloxycarbonyl
Fmoc is 9-fluorenylmethoxycarbonyl
Chg is L-cyclohexylglycyl
Nle is L-norleucinyl
Hyn is L-6-hydroxynorleucinyl

Example 17

Preparation of N-Cbz-Gly-Pro-Melphalan

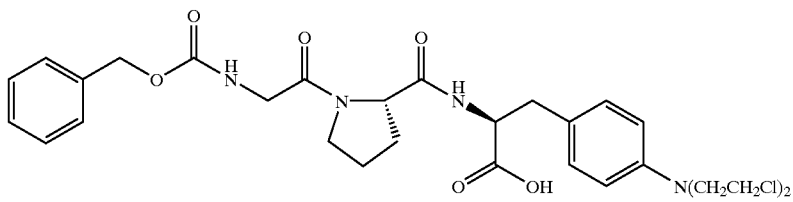

N-Cbz-Gly-Pro-OH (22 mg, 0.072 mmol) was dissolved in anhydrous N,N-dimethylformamide (8 ml) and pH was adjusted to 7.5 by N,N-diisopropylethylamine. N-hydroxysuccinimide (1 M in DMF, 72 µl, 0.072 mmol) was added and the mixture was cooled in an ice bath. Under stirring, dicyclohexylcarbodiimide (1 M in DMF, 67 µl, 0.67 mmol) was added and the solution was stirred at 0° C. for 2 h.

Melphalan (14.7 mg, 0.048 mmol) was dissolved in 30 ml anhydrous DMF and N,N-duisopropylethylamine (12.3 µl, 0.072 mmol) was added. This mixture was syringed to the activated peptide. The reaction was allowed to warm up to room temperature and was stirred for 24 h.

The solvent was then removed and the product was purified by preparative RP-HPLC on C18 using a gradient of water/acetonitrile with 0.1% trifluoracetic acid.

Analytical data: HPLC >90%, ES-MS 593.0 ([M+H]$^+$).

SEQUENCE LISTING

<160> NUMBER OF SEQ ID NOS: 28

<210> SEQ ID NO 1
<211> LENGTH: 4
<212> TYPE: PRT
<213> ORGANISM: Artificial Sequence
<220> FEATURE:
<223> OTHER INFORMATION: FAP binding cytotoxic compound protein
      conjugate
<220> FEATURE:
<221> NAME/KEY: MISC_FEATURE
<222> LOCATION: (1)..(4)
<223> OTHER INFORMATION: N terminal blocking group, C terminally linked
      to doxorubicin

<400> SEQUENCE: 1

Pro Ala Gly Pro
1

<210> SEQ ID NO 2
<211> LENGTH: 4
<212> TYPE: PRT
<213> ORGANISM: Artificial Sequence
<220> FEATURE:
<223> OTHER INFORMATION: FAP binding cytotoxic compound protein
      conjugate
<220> FEATURE:
<221> NAME/KEY: MISC_FEATURE
<222> LOCATION: (1)..(4)
<223> OTHER INFORMATION: N terminal blocking group, C terminally linked
      to doxorubicin

<400> SEQUENCE: 2

Lys Ala Gly Pro
1

<210> SEQ ID NO 3
<211> LENGTH: 4
<212> TYPE: PRT
<213> ORGANISM: Artificial Sequence
<220> FEATURE:
<223> OTHER INFORMATION: FAP binding cytotoxic compound protein
      conjugate
<220> FEATURE:
<221> NAME/KEY: MISC_FEATURE
<222> LOCATION: (1)..(4)
<223> OTHER INFORMATION: N terminal amino acid is 3HyP with blocking
      group, C terminally linked to doxorubicin

<400> SEQUENCE: 3

Pro Ala Gly Pro
1

<210> SEQ ID NO 4
<211> LENGTH: 4
<212> TYPE: PRT
<213> ORGANISM: Artificial Sequence
<220> FEATURE:
<223> OTHER INFORMATION: Precursor peptide to SEQ ID #1
<220> FEATURE:
<221> NAME/KEY: MISC_FEATURE
<222> LOCATION: (1)..(4)
<223> OTHER INFORMATION: N terminal blocking group

<400> SEQUENCE: 4

Pro Ala Gly Pro
1

```
<210> SEQ ID NO 5
<211> LENGTH: 4
<212> TYPE: PRT
<213> ORGANISM: Artificial Sequence
<220> FEATURE:
<223> OTHER INFORMATION: Artificial test peptide containing MNA to test
      for FAP activity
<220> FEATURE:
<221> NAME/KEY: MISC_FEATURE
<222> LOCATION: (1)..(4)
<223> OTHER INFORMATION: Contains Pro-methoxy-beta-napthylamide

<400> SEQUENCE: 5

Pro Ala Gly Pro
1

<210> SEQ ID NO 6
<211> LENGTH: 4
<212> TYPE: PRT
<213> ORGANISM: Artificial Sequence
<220> FEATURE:
<223> OTHER INFORMATION: Contains Fmoc
<220> FEATURE:
<221> NAME/KEY: MISC_FEATURE
<222> LOCATION: (1)..(4)
<223> OTHER INFORMATION: N terminally linked to
      9-fluorenylmethoxycarbonyl (Fmoc)

<400> SEQUENCE: 6

Pro Ala Gly Pro
1

<210> SEQ ID NO 7
<211> LENGTH: 4
<212> TYPE: PRT
<213> ORGANISM: Artificial Sequence
<220> FEATURE:
<223> OTHER INFORMATION: Contains Fmoc
<220> FEATURE:
<221> NAME/KEY: MISC_FEATURE
<222> LOCATION: (1)..(4)
<223> OTHER INFORMATION: N-terminally linked to Fmoc
<220> FEATURE:
<221> NAME/KEY: MISC_FEATURE
<222> LOCATION: (3)..(3)
<223> OTHER INFORMATION: Amino acid 3 is Xaa wherein Xaa =
      L-6-hydroxynorleucinyl; N-linked to Fmoc

<400> SEQUENCE: 7

Ser Ala Xaa Pro
1

<210> SEQ ID NO 8
<211> LENGTH: 4
<212> TYPE: PRT
<213> ORGANISM: Artificial Sequence
<220> FEATURE:
<223> OTHER INFORMATION: Contains Fmoc
<220> FEATURE:
<221> NAME/KEY: MISC_FEATURE
<222> LOCATION: (1)..(4)
<223> OTHER INFORMATION: N-terminally linked to Fmoc
<220> FEATURE:
<221> NAME/KEY: MISC_FEATURE
<222> LOCATION: (3)..(3)
<223> OTHER INFORMATION: Amino acid 3 is Xaa wherein Xaa = L-norleucinyl

<400> SEQUENCE: 8

Ser Ala Xaa Pro
1
```

```
<210> SEQ ID NO 9
<211> LENGTH: 4
<212> TYPE: PRT
<213> ORGANISM: Artificial Sequence
<220> FEATURE:
<223> OTHER INFORMATION: Contains Fmoc
<220> FEATURE:
<221> NAME/KEY: MISC_FEATURE
<222> LOCATION: (1)..(4)
<223> OTHER INFORMATION: N-terminally linked to Fmoc
<220> FEATURE:
<221> NAME/KEY: MISC_FEATURE
<222> LOCATION: (3)..(3)
<223> OTHER INFORMATION: Amino acid 3 is Xaa wherein Xaa =
      L-cyclohexylglycyl

<400> SEQUENCE: 9

Ser Ala Xaa Pro
1

<210> SEQ ID NO 10
<211> LENGTH: 5
<212> TYPE: PRT
<213> ORGANISM: Artificial Sequence
<220> FEATURE:
<223> OTHER INFORMATION: Precursor

<400> SEQUENCE: 10

Gly Ser Ala Glu Pro
1               5

<210> SEQ ID NO 11
<211> LENGTH: 6
<212> TYPE: PRT
<213> ORGANISM: Artificial Sequence
<220> FEATURE:
<223> OTHER INFORMATION: Precursor

<400> SEQUENCE: 11

Gly Gly Ser Ala Glu Pro
1               5

<210> SEQ ID NO 12
<211> LENGTH: 7
<212> TYPE: PRT
<213> ORGANISM: Artificial Sequence
<220> FEATURE:
<223> OTHER INFORMATION: Precursor

<400> SEQUENCE: 12

Gly Gly Gly Ser Ala Glu Pro
1               5

<210> SEQ ID NO 13
<211> LENGTH: 7
<212> TYPE: PRT
<213> ORGANISM: Artificial Sequence
<220> FEATURE:
<223> OTHER INFORMATION: Precursor

<400> SEQUENCE: 13

Ser Glu Asn Arg Lys Val Pro
1               5

<210> SEQ ID NO 14
<211> LENGTH: 6
<212> TYPE: PRT
<213> ORGANISM: Artificial Sequence
<220> FEATURE:
```

<223> OTHER INFORMATION: Precursor

<400> SEQUENCE: 14

Gly Tyr Ser Arg Met Pro
1               5

<210> SEQ ID NO 15
<211> LENGTH: 7
<212> TYPE: PRT
<213> ORGANISM: Artificial Sequence
<220> FEATURE:
<223> OTHER INFORMATION: Precursor

<400> SEQUENCE: 15

Gln Gly Tyr Ser Arg Met Pro
1               5

<210> SEQ ID NO 16
<211> LENGTH: 5
<212> TYPE: PRT
<213> ORGANISM: Artificial Sequence
<220> FEATURE:
<223> OTHER INFORMATION: Precursor

<400> SEQUENCE: 16

Gly Gly Gly Trp Pro
1               5

<210> SEQ ID NO 17
<211> LENGTH: 5
<212> TYPE: PRT
<213> ORGANISM: Artificial Sequence
<220> FEATURE:
<223> OTHER INFORMATION: Precursor

<400> SEQUENCE: 17

Asn Arg Lys Val Pro
1               5

<210> SEQ ID NO 18
<211> LENGTH: 6
<212> TYPE: PRT
<213> ORGANISM: Artificial Sequence
<220> FEATURE:
<223> OTHER INFORMATION: Precursor

<400> SEQUENCE: 18

Glu Asn Arg Lys Val Pro
1               5

<210> SEQ ID NO 19
<211> LENGTH: 7
<212> TYPE: PRT
<213> ORGANISM: Artificial Sequence
<220> FEATURE:
<223> OTHER INFORMATION: Precursor

<400> SEQUENCE: 19

Ser Glu Asn Arg Lys Val Pro
1               5

<210> SEQ ID NO 20
<211> LENGTH: 5
<212> TYPE: PRT
<213> ORGANISM: Artificial Sequence
<220> FEATURE:
<223> OTHER INFORMATION: Precursor

```
<400> SEQUENCE: 20

Ala His Met His Pro
1               5

<210> SEQ ID NO 21
<211> LENGTH: 5
<212> TYPE: PRT
<213> ORGANISM: Artificial Sequence
<220> FEATURE:
<223> OTHER INFORMATION: Precursor

<400> SEQUENCE: 21

Tyr Ala Phe His Pro
1               5

<210> SEQ ID NO 22
<211> LENGTH: 6
<212> TYPE: PRT
<213> ORGANISM: Artificial Sequence
<220> FEATURE:
<223> OTHER INFORMATION: Precursor

<400> SEQUENCE: 22

Ser Tyr Ala Phe His Pro
1               5

<210> SEQ ID NO 23
<211> LENGTH: 6
<212> TYPE: PRT
<213> ORGANISM: Artificial Sequence
<220> FEATURE:
<223> OTHER INFORMATION: Precursor

<400> SEQUENCE: 23

Leu Asn Leu Tyr Met Pro
1               5

<210> SEQ ID NO 24
<211> LENGTH: 5
<212> TYPE: PRT
<213> ORGANISM: Artificial Sequence
<220> FEATURE:
<223> OTHER INFORMATION: Precursor

<400> SEQUENCE: 24

Gly Ser Ala Glu Pro
1               5

<210> SEQ ID NO 25
<211> LENGTH: 6
<212> TYPE: PRT
<213> ORGANISM: Artificial Sequence
<220> FEATURE:
<223> OTHER INFORMATION: Precursor

<400> SEQUENCE: 25

Gly Gly Ser Ala Glu Pro
1               5

<210> SEQ ID NO 26
<211> LENGTH: 7
<212> TYPE: PRT
<213> ORGANISM: Artificial Sequence
<220> FEATURE:
<223> OTHER INFORMATION: Precursor
```

```
<400> SEQUENCE: 26

Gly Gly Gly Ser Ala Glu Pro
1               5

<210> SEQ ID NO 27
<211> LENGTH: 6
<212> TYPE: PRT
<213> ORGANISM: Artificial Sequence
<220> FEATURE:
<223> OTHER INFORMATION: SEQ ID 151 of WO 97/12624
<220> FEATURE:
<221> NAME/KEY: MISC_FEATURE
<222> LOCATION: (1)..(1)
<223> OTHER INFORMATION: Amino acid 1 is Xaa wherein Xaa = hArg

<400> SEQUENCE: 27

Xaa Tyr Gln Ser Ser Pro
1               5

<210> SEQ ID NO 28
<211> LENGTH: 5
<212> TYPE: PRT
<213> ORGANISM: Artificial Sequence
<220> FEATURE:
<223> OTHER INFORMATION: SEQ NO 177 of WO 97/14416
<220> FEATURE:
<221> NAME/KEY: MISC_FEATURE
<222> LOCATION: (1)..(1)
<223> OTHER INFORMATION: Amino acid 1 is Xaa wherein Xaa = hArg

<400> SEQUENCE: 28

Xaa Tyr Gln Ser Pro
1               5
        1-1087 US.ST25
        Page 1
```

What is claimed is:

1. A compound of formula (I)

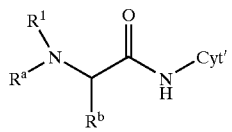

(I)

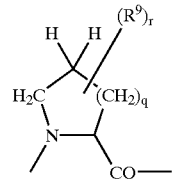

or a pharmaceutically acceptable salt thereof, wherein $R^1$ represents a residue of formula Cg—A, Cg—B—A or Cg—(D)$_m$—B—A, in which Cg represents a capping group selected from the group consisting of $R^5$—CO, $R^5$—O—CO—, $R^5$—NH—CO—, $R^5$—SO$_2$— or $R^5$—, wherein $R^5$ is an optionally substituted $C_3$–$C_8$-cycloalkyl, aryl, aralkyl or heteroaryl group;

A is an amino carboxylic acid moiety selected from L-proline, glycine, L-norleucine, L-cyclohexylglycine, L-5-hydroxynorleucine, L-6-hydroxynorleucine, L-5-hydroxylysine, L-arginine, and L-lysine; and B and D each independently represent an amino carboxylic moiety of the formula —[NR$^6$—(X)$_p$—CO]— wherein X represents CR$^7$R$^8$ and wherein $R^6$, $R^7$ and $R^8$ each independently represent a hydrogen atom, an optionally substituted $C_1$–$C_6$-alkyl, $C_3$–$C_8$-cycloalkyl, aryl or heteroaryl group, and p is 1, 2, 3, 4 or 5; or B and D each independently represent moieties derived from cyclic amino carboxylic acids of formula wherein $R^9$ represents $C_1$–$C_6$-alkyl, OH, or NH$_2$, m is an integer from 1 to 10;

q is 0, 1 or 2; and r is 0, 1 or 2;

$R^a$ and $R^b$ together with the interjacent N—C group form an optionally substituted, optionally benzo- or cyclohexano-condensed 3- to 7-membered saturated or unsaturated heterocyclic ring, in which one or two CH$_2$ groups may also be replaced by NH, O or S, and —NH—Cyt' represents a cytotoxic compound or cytostatic compound, less a hydrogen atom.

2. The compound of formula I according to claim 1, wherein the heterocyclic ring formed by $R^a$, $R^b$ and the interjacent N—C is substituted by $R^2$ and $R^3$, wherein $R^2$ and $R^3$ each independently represent hydrogen, halogen atom, $C_1$–$C_6$-alkyl, $C_1$–$C_6$-alkylamino, di-$C_1$–$C_6$-alkylamino, $C_1$–$C_6$-alkoxy, thiol, $C_1$–$C_6$-alkylthio, oxo, imino, fomlyl, $C_1$–$C_6$-alkoxy carbonyl, amino carbonyl, $C_3$—$C_8$-cycloalkyl, aryl or heteroaryl group.

3. A compound of formula IA

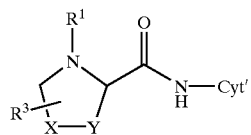

(IA)

wherein $R^1$ and —NH—Cyt' are as defined in claimed, and $R^2$ and $R^3$ are as defined in claim 2, X—Y represents $CHR^2$—$CH_2$, $CR^2$=CH, NH—$CH_2$, $CH_2$—NH, —$CR^2$— or $CH_2$—$CHR^2$—$CH_2$.

4. A compound of formula IA1

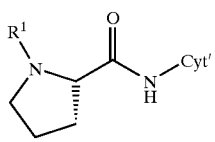

(IA1)

wherein $R^1$ and —NH—Cyt' are as defined in claim 1.

5. A compound selected from the formulae IA2, IA3, IA4 and IA5

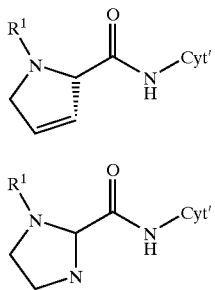

(IA2)

(IA3)

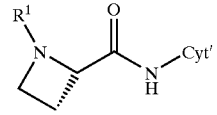

(IA4)

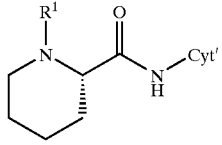

(IA5)

wherein $R^1$ and —NH—Cyt' are defined in claim 1.

6. The compound according to claim 1 wherein $R^1$ is a group selected from
  Cg-Gly,
  Cg-Nle and
  Cg-(Xaa)$_m$-Xaa-Gly;

Cg represents a hydrogen atom or a capping group selected from benzoyloxycarbonyl, phenylacetyl, phenylmethylsulfonyl and benzylaminocarbonyl;

Xaa represents an amino carboxylic acid moiety and m is an integer from 1 to 6.

7. The compound according to claim 6 wherein the amino carboxylic acid moieties exist in the (L)-configuration.

8. A compound according to claim 1 wherein —HN—Cyt' is an anthracycline derivative.

9. A compound according to claim 8 selected from the formulae (IIIA), (IIIB), (IIIE) and (IIIF):

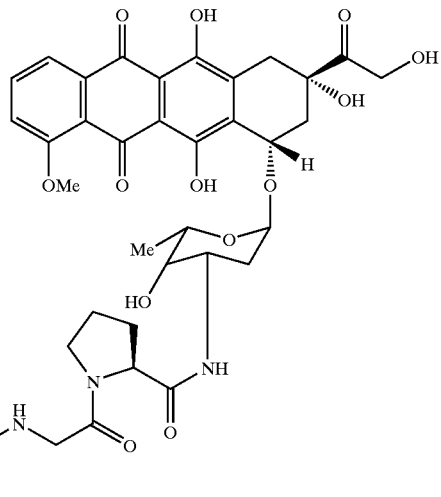

(IIIA)

-continued
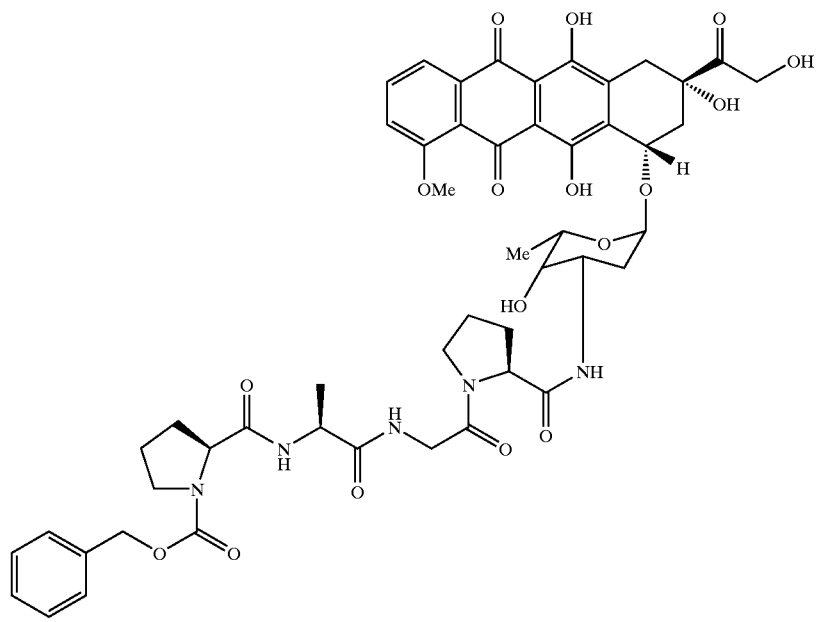
(IIIB)
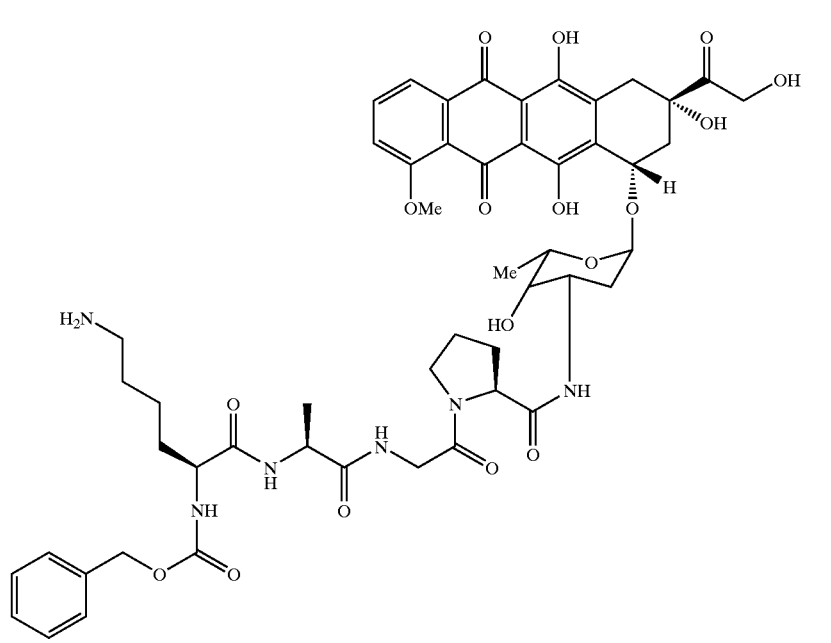
(IIIE)

-continued

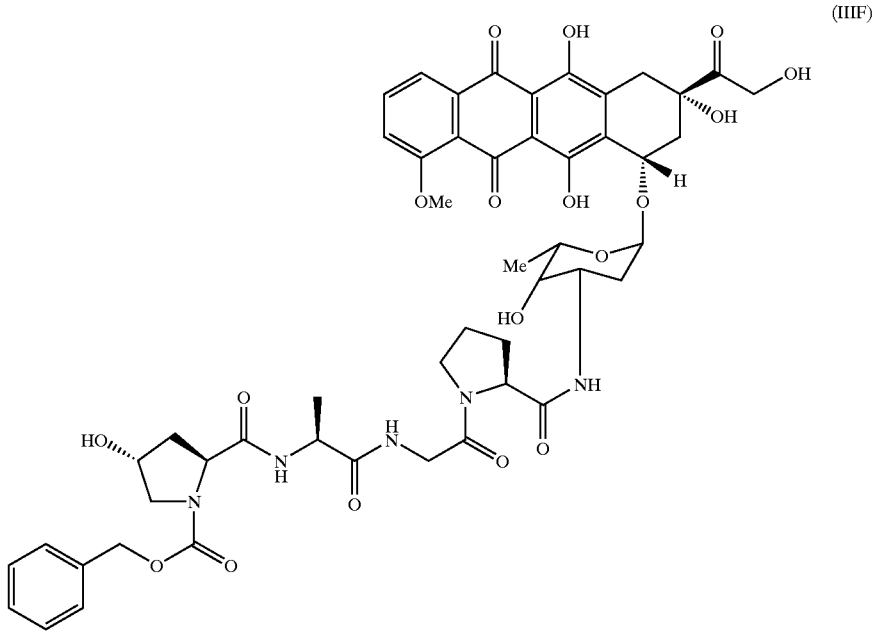
(IIIF)

10. A pharmaceutical composition comprising a compound according to claim 1 in combination with a pharmaceutically acceptable carrier.

11. A process for the production of a compound of formula I according to claim 1,

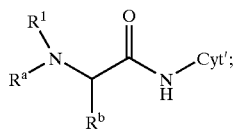
(I)

said process comprising
reacting a compound of formula (V)

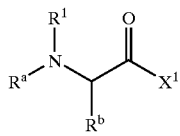
(V)

wherein $R^1$, $R^a$ and $R^b$ are as defined in claim 31, $X^1$ is hydroxy or a leaving group
which is suitable to be substituted by an amino group, with a cytotoxic or cytostatic compound $H_2N$—Cyt′, and isolating the resulting final product compound of the formula (I).

12. A method of treatment of cancer, comprising administering to a patient in need thereof a pharmaceutical composition according to claim 10 for a time and under conditions effective to inhibit proliferation of tumor cells.

13. A method of treatment of cancer comprising administering to a patient in need thereof a compound according to claim 1 in an amount effective to inhibit proliferation of tumor cells cells and for a time and under conditions effective to inhibit proliferation of tumor cells.

14. A method of treating a disease chosen from epithelial carcinomas chosen from breast, lung, colorectal, head and neck, pancreatic, ovarian, bladder, gastric, skin, endometrial, ovarian, testicular, esophageal, prostatic and renal origin;

bone and soft-tissue sarcomas chosen from osteosarcoma, chondrosarcoma, fibrosarcorma, malignant fibrous histiocytoma (MFH) and leiomyosarcoma;

hematopoietic malignancies chosen from Hodgkin's and non-Hodgkin's lymphomas; neuroectodermal tumors chosen from peripheral nerve tumors, astrocytomas and melanomas;

and mesotheliomas cancer comprising administering to a patient in need thereof a compound according to claim 1 in an amount effective to inhibit proliferation of tumor cells.

* * * * *